US012390162B2

(12) United States Patent
Dana et al.

(10) Patent No.: US 12,390,162 B2
(45) Date of Patent: Aug. 19, 2025

(54) METHOD AND DEVICE FOR WEARABLE CONTACT LENSES FOR REMOTE OPTICAL MONITORING OF INTRAOCULAR PRESSURE

(71) Applicant: SmartLens, Inc., Santa Clara, CA (US)

(72) Inventors: Aykutlu Dana, Santa Clara, CA (US); Sevda Agaoglu, Santa Clara, CA (US); Ahmet Taylan Yazici, Santa Clara, CA (US); Sencer Ayas, Santa Clara, CA (US); Murat Baday, Santa Clara, CA (US); Savas Komban, Santa Clara, CA (US)

(73) Assignee: SMARTLENS, INC., Mountain View, CA (US)

(*) Notice: Subject to any disclaimer, the term of this patent is extended or adjusted under 35 U.S.C. 154(b) by 977 days.

(21) Appl. No.: 17/344,841

(22) Filed: Jun. 10, 2021

(65) Prior Publication Data
US 2021/0298677 A1 Sep. 30, 2021

Related U.S. Application Data

(63) Continuation of application No. PCT/US2019/066512, filed on Dec. 16, 2019.
(Continued)

(51) Int. Cl.
*A61B 5/00* (2006.01)
*A61B 3/16* (2006.01)
*B29D 11/00* (2006.01)

(52) U.S. Cl.
CPC ............. *A61B 5/6821* (2013.01); *A61B 3/16* (2013.01); *B29D 11/00038* (2013.01);
(Continued)

(58) Field of Classification Search
USPC ...................................... 156/308.6
See application file for complete search history.

(56) References Cited

U.S. PATENT DOCUMENTS

| 3,228,741 A | 1/1966 | Becker |
| 5,840,041 A | 11/1998 | Petter et al. |

(Continued)

FOREIGN PATENT DOCUMENTS

| CN | 103415244 A | 11/2013 |
| CN | 204394461 U | 6/2015 |

(Continued)

OTHER PUBLICATIONS

Co-pending U.S. Appl. No. 17/875,719, inventors Dana; Aykutlu et al., filed Jul. 28, 2022.
(Continued)

*Primary Examiner* — Abbas Rashid
*Assistant Examiner* — Gregory C. Grosso
(74) *Attorney, Agent, or Firm* — WILSON SONSINI GOODRICH & ROSATI

(57) ABSTRACT

A contact lens with a sensor region are described. The contact allows for normal vision and a concentric ring around the vision area of the lens includes one or more sensors for detecting changes in the interocular pressure of the eye. The data may be scanned using a camera, or in some embodiments, the data may be transmitted using a micro antenna in the sensing region. The data may be analyzed using a software application on a cell phone or other computing device.

16 Claims, 47 Drawing Sheets

Related U.S. Application Data

(60) Provisional application No. 62/780,128, filed on Dec. 14, 2018.

(52) U.S. Cl.
CPC .. *B29D 11/00865* (2013.01); *B29D 11/00932* (2013.01); *A61B 2562/12* (2013.01)

(56) References Cited

U.S. PATENT DOCUMENTS

| | | |
|---|---|---|
| 6,645,432 B1 | 11/2003 | Anderson et al. |
| 6,686,184 B1 | 2/2004 | Anderson et al. |
| 7,267,938 B2 | 9/2007 | Anderson et al. |
| 7,531,120 B2 | 5/2009 | Van Rijn et al. |
| 7,670,556 B2 | 3/2010 | Corn et al. |
| 7,835,013 B2 | 11/2010 | Jones et al. |
| 7,887,508 B2 | 2/2011 | Meng et al. |
| 7,927,783 B2 | 4/2011 | Aizenberg et al. |
| 7,981,097 B2 | 7/2011 | Paoli, Jr. |
| 8,088,615 B2 | 1/2012 | Ausserre |
| 8,124,029 B2 | 2/2012 | Polwart et al. |
| 8,220,494 B2 | 7/2012 | Studer et al. |
| 8,263,129 B2 | 9/2012 | DeSimone et al. |
| 8,308,686 B2 | 11/2012 | Meng et al. |
| 8,850,895 B2 | 10/2014 | Yan et al. |
| 8,985,763 B1 | 3/2015 | Etzkorn et al. |
| 9,046,641 B2 | 6/2015 | Lai et al. |
| 9,289,123 B2 | 3/2016 | Weibel et al. |
| 9,964,780 B2 | 5/2018 | Pugh et al. |
| 9,977,258 B2 | 5/2018 | Pugh et al. |
| 10,016,132 B2 | 7/2018 | Mandel et al. |
| 10,085,637 B2 | 10/2018 | Araci et al. |
| 10,139,522 B2 | 11/2018 | Marullo et al. |
| 10,219,696 B2 | 3/2019 | Araci et al. |
| 10,898,074 B2 | 1/2021 | Araci et al. |
| 11,213,203 B2 | 1/2022 | Mandel et al. |
| 11,759,107 B2 | 9/2023 | Araci et al. |
| 2002/0052544 A1 | 5/2002 | Jeffries et al. |
| 2004/0169932 A1 | 9/2004 | Esch et al. |
| 2004/0254438 A1 | 12/2004 | Chuck et al. |
| 2006/0055884 A1 | 3/2006 | Molinari et al. |
| 2009/0076367 A1 | 3/2009 | Sit et al. |
| 2010/0016704 A1 | 1/2010 | Naber et al. |
| 2011/0015512 A1 | 1/2011 | Pan et al. |
| 2012/0253165 A1 | 10/2012 | Yen et al. |
| 2013/0041245 A1 | 2/2013 | Cerboni |
| 2013/0055819 A1* | 3/2013 | Yan .................. B29D 11/0073 73/705 |
| 2013/0184554 A1 | 7/2013 | Elsheikh et al. |
| 2013/0253451 A1 | 9/2013 | Kim |
| 2013/0278887 A1 | 10/2013 | Legerton |
| 2014/0163351 A1 | 6/2014 | Wang et al. |
| 2014/0197558 A1 | 7/2014 | Linhardt et al. |
| 2014/0243645 A1 | 8/2014 | Leonardi |
| 2014/0343387 A1 | 11/2014 | Pugh et al. |
| 2014/0354942 A1 | 12/2014 | Pugh et al. |
| 2015/0057593 A1 | 2/2015 | Johnson et al. |
| 2015/0148648 A1 | 5/2015 | Pugh |
| 2015/0164321 A1 | 6/2015 | Weibel et al. |
| 2016/0007851 A1 | 1/2016 | Araci et al. |
| 2016/0015265 A1 | 1/2016 | Mandel et al. |
| 2016/0051143 A1 | 2/2016 | Rickard et al. |
| 2016/0262616 A1 | 9/2016 | Araci et al. |
| 2016/0270656 A1 | 9/2016 | Samec et al. |
| 2017/0000341 A1 | 1/2017 | Samec et al. |
| 2017/0165439 A1 | 6/2017 | Kaufmann |
| 2017/0181626 A1 | 6/2017 | Shau et al. |
| 2017/0184875 A1 | 6/2017 | Newman |
| 2017/0280997 A1 | 10/2017 | Lai et al. |
| 2018/0279870 A1 | 10/2018 | Walsh et al. |
| 2018/0296390 A1 | 10/2018 | Hoare |
| 2019/0076021 A1* | 3/2019 | Araci .................. A61B 3/16 |
| 2020/0138669 A1 | 5/2020 | Berdahl et al. |
| 2021/0113083 A1 | 4/2021 | Araci et al. |
| 2022/0022744 A1 | 1/2022 | Dana et al. |
| 2023/0380686 A1 | 11/2023 | Araci et al. |

FOREIGN PATENT DOCUMENTS

| | | |
|---|---|---|
| CN | 105934194 A | 9/2016 |
| CN | 105962887 A | 9/2016 |
| CN | 105962887 B | 9/2017 |
| CN | 107908015 A | 4/2018 |
| JP | H06289333 A | 10/1994 |
| JP | 2010201621 A | 9/2010 |
| JP | 2013541049 A | 11/2013 |
| JP | 2016527561 A | 9/2016 |
| JP | 2018517929 A | 7/2018 |
| JP | 2018518700 A | 7/2018 |
| WO | WO-9743614 A1 | 11/1997 |
| WO | WO-2016173554 A1 | 11/2016 |
| WO | WO-2017182817 A1 | 10/2017 |
| WO | WO-2018221687 A1 | 12/2018 |
| WO | WO-2019175667 A1 | 9/2019 |
| WO | WO-2020060558 A1 | 3/2020 |
| WO | WO-2020124074 A1 | 6/2020 |
| WO | WO-2020146714 A1 | 7/2020 |
| WO | WO-2020210322 A1 | 10/2020 |
| WO | WO-2021154729 A1 | 8/2021 |
| WO | WO-2022182629 A1 | 9/2022 |

OTHER PUBLICATIONS

EP18934447.6 Extended Search Report dated Mar. 10, 2022.
EP19894568.5 Extended Search Report dated Aug. 8, 2022.
EP20738775.4 Extended Search Report dated Sep. 6, 2022.
PCT/US2022/017224 International Search Report and Written Opinion dated May 11, 2022.
Agaouglu et al. Ultra-sensitive microfluidic wearable strain sensor for intraocular pressure monitoring. Lab on a Chip, Issue 22, 2018; pp. 3471-3483.
Chen et al., Soft wearable contact lens sensor for continuous intraocular pressure monitoring, Medical Engineering & Physics, vol. 36, Issue 9, Sep. 2014, pp. 1134-1139.
Co-pending U.S. Appl. No. 17/370,735, inventors Dana; Aykutlu et al., filed Jul. 8, 2021.
International Search Report for PCT/US2020/027221 on Jun. 19, 2020.
International Search Report and Written Opinion for PCT/US2019/066512 on Apr. 14, 2020.
Kim et al., Wearable smart sensor systems integrated on soft contact lenses for wireless ocular diagnostics, Nature Communications, vol. 8, Apr. 27, 2017, Article No. 14997.
Notice of allowance dated Oct. 6, 2020 for U.S. Appl. No. 16/124,630.
Office action dated Aug. 11, 2020 for U.S. Appl. No. 16/124,630.
PCT/US2018/052062 International Search Report and Written Opinion of the Searching Authority dated Dec. 11, 2018.
PCT/US2020/013049 International Search Report and Written Opinion of the International Searching Authority dated Mar. 19, 2020.
PCT/US2021/015093 International Search Report & Written Opinion of the International Searching Authority dated Jun. 3, 2021.
U.S. Appl. No. 13/330,681 Notice of Allowance dated Jul. 7, 2014.
U.S. Appl. No. 13/330,681 Office Action dated Mar. 12, 2014.
U.S. Appl. No. 15/067,378 Notice of Allowance dated Jul. 9, 2018.
Co-pending U.S. Appl. No. 18/500,766, inventors Araci; Ismail Emre et al., filed Nov. 2, 2023.
U.S. Appl. No. 16/124,630 Corrected Notice of Allowability dated Nov. 23, 2020.
U.S. Appl. No. 17/137,067 Notice of Allowance dated May 19, 2023.
U.S. Appl. No. 17/137,067 Office Action dated Nov. 2, 2022.

* cited by examiner

METHOD AND DEVICE FOR WEARABLE CONTACT LENSES FOR REMOTE OPTICAL MONITORING OF INTRAOCULAR PRESSURE

CROSS-REFERENCE TO RELATED APPLICATIONS

This application is a continuation of PCT Application No. PCT/US19/66512, filed Dec. 16, 2019, which claims priority from U.S. Provisional Application 62/780,128 entitled "Method and Devices for Wearable Contact Lenses for Monitoring Interocular Pressure" filed Dec. 14, 2018, the contents of which are hereby incorporated by reference in their entirety.

BACKGROUND

Field

The present disclosure relates to micromachined sensors. More particularly, the present disclosure relates to wearable microfluidic, optical, electronic and electromagnetic sensors for measuring the intraocular pressure (IOP) and corneal temperature.

Background

Glaucoma is the second most common cause of blindness in the global world. It is a multifactorial disease with several risk factors, of which intraocular pressure (IOP) is the most important. IOP measurements are used for glaucoma diagnosis and patient monitoring. IOP has wide diurnal fluctuation, and is dependent on body posture and several other factors, so the occasional measurements done by the eye care expert in clinic can be insufficient and misleading.

Previously (US20160015265A1, 2018), an implantable microfluidic device has been proposed for intraocular pressure monitoring, that can be used for glaucoma diagnosis. Later, a wearable device was proposed (US2019/076021A1, 2019) to serve the same purpose, however without needing implantation.

BRIEF SUMMARY

The present disclosure relates to a contact lens with a sensor for detecting changes in the intraocular pressure (IOP) of an eye. The sensor may utilize software technology in the form of a mobile device app to analyze the sensor data, which may be presented in visual, radio or thermal manner.

In various embodiments, the contact lens may be formed from two polymer assemblies put together like a sandwich. The two polymer assemblies work cooperatively to form a single contact lens with IOP sensor. In other embodiments, various methods of making the molds used to make the contact lens with IOP sensor are described. In other embodiments, various forms of the IOP sensor are described, as well as other forms of sensors relating to the eye.

In an embodiment, there may be a method or producing a planar mold. The method involves fabricating a planar substrate from a silicon material. Creating one or more reliefs on the planar surface wherein the reliefs will create one or more microfluidic channels in a membrane sheet.

In an embodiment, there may be a method of producing a mold for use in the fabrication of a contact lens with a sensor. The method involves placing a liquid material on a planar mold, the liquid material being capable of changing from a liquid state to a substantially solid state. The planar mold may impart one or more microfluidic channels to the liquid material as the material transitions to the substantially solid state. The substantially solid state of the material forms a membrane sheet. Then centering a holder on to the membrane sheet, excising a portion of the membrane sheet, the portion of the membrane sheet having the microfluidic channels, the portion of the membrane forming the membrane template. The membrane template is then clamped between the holder and a base assembly. The base assembly may have an aperture or a hole in the middle. The holder may be removed from the base assembly so the membrane template remains on the base assembly. The base assembly may then be pressed on to a curved mold, such that the membrane template is pressed against the curved mold. The base assembly aperture may then be filled with additional liquid material. The additional liquid material may be cured, and the resulting cured material forms a mold that has a curved surface that matches the curvature of the curved mold. The cured mold may be separated from the curved mold.

In another embodiment, there may be a method of producing a curved mold for making a contact lens with a sensor, the method involves coating a curved mold with a photoresist and curing the photoresist. Then creating a predefined pattern in the photoresist. The pattern is developed and an elastomer is poured on top of the developed pattern. The photoresist is then cured to produce a mold.

In another embodiment, there may be a method for producing a contact lens and sensor apparatus. The method involves forming a bottom membrane layer by coating a curved mold with a liquid elastomer and curing it. Then treating the bottom membrane layer with plasma to make the elastomeric surface hydrophilic and promote adhesion of a UV curable polymer. Then coating the elastomeric surface with a UV curable polymer, and imprinting microfluidic layers on the UV curable polymer using a mold. The method also involves as a separate process, making a top membrane layer by pouring elastomer on to a second curved mold, curing the top membrane layer and releasing the top membrane layer after curing it. Then performing a plasma treatment on the inside of the top membrane, coating the inside of the top membrane with UV curable polymer, and partially curing to solidify the UV curable polymer. Then placing the top membrane onto a pressurizing chamber, bonding the top and bottom membranes together to form a contact lens and sensor template and cutting the contact lens and sensor template to size. The cutting forms an abrupt edge on the contact lens, so a UV curable polymer is applied to the abrupt edge of the contact lens to form an atraumatic edge.

In an embodiment, there may be an apparatus for measuring the intraocular pressure of an eye, the apparatus including an elastomeric contact lens body and a plurality of metallized Fabry-Perot optical interference cavities, the cavities distributed around the vision portion of the contact lens wherein changes of shape and reflected light cause changes in the contact lens' shape due to changes in intraocular pressure.

In an embodiment, there may be an apparatus for measuring the intraocular pressure of an eye. The apparatus has an elastomeric contact lens body and a group of metallized cavities distributed in a sensor region of a contact lens body. The plurality of metallized cavities act as mechanically variable capacitors and resonating antennas within the contact lens and the group of metallized cavities change electromagnetic resonant response properties upon changes in intraocular pressure, by changing in capacitance or by changes in direct electrical contact between different parts of the antennas.

In an embodiment, there may be an apparatus for measuring the intraocular pressure (IOP) of an eye. The apparatus may have an elastomeric contact lens body with a sensor region. There may be embedded transmission type gratings in the sensor region. The grating permitting external light into the posterior corneal cavity. Input and output coupling gratings route the external light, wherein the coupling condition on angle of incidence and wavelength of light can be used to calculate the strain exerted on the contact lens.

In an embodiment, there may be an apparatus for measuring the intraocular pressure of an eye. The apparatus may have an elastomeric contact lens body having a sensor region. There may be fluorescent beads embedded into the sensor region.

In an embodiment, there may be a system for determining changes in intraocular pressure over time. The system may include an elastomeric microfluidic contact lens with a sensor region. Microfluidic channels may be dispersed within the sensor region. The channels may contain a density sensitive material capable of adhering to the microfluidic walls. The system may also have an optical reader for reading the changes in the density sensitive material, wherein the changes in density of the density sensitive material corresponds to changes in the intraocular pressure of the eye. Reading the optical density changes on the walls can be used to calculate intraocular pressure. The density sensitive material may be a dye, or fluorescent beads.

In another embodiment, there may be an apparatus for measuring the intraocular pressure of an eye. The apparatus may have an elastomeric microfluidic contact lens with a sensor region. Liquid crystal thermometers may be embedded in the sensor region, wherein the liquid crystal thermometers change color due to corneal temperature changes.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Described herein are various embodiments for a contact lens and IOP sensor, various molds and methods of making the same. The contact lens may be one that may be used for vision correction, cosmetic appearance or having no vision correction and no cosmetic effect. The portion of the contact lens that may lay over that portion of the eye a person (or animal) may see through may be visually transparent, and otherwise not interfere with the vision of the eye. This center portion of the device may be referred to as the vision area. The lens area may provide proper vision correction, aesthetic color or simply be transparent.

In various embodiments, the sensor portion of the contact lens may have one or more elements embedded in the periphery of the contact lens. The periphery may be thought of as the annular space around the vision area of the contact lens. The periphery area may be thought of as the sensor area.

The contact lens with sensor may be constructed in a variety of ways. In an embodiment, it may be possible to take an existing contact lens and add a sensor area around it. In another embodiment, it may be possible to construct a vision/aesthetic lens and a sensor area at the same time.

Described herein are numerous embodiments for creating a top and bottom layer vision and sensor area and then putting the two layers together to form a single contact lens with sensor. In various embodiments, there may be a mold for the top layer and another mold for the bottom layer. Numerous methods of making the two molds as well as for making the two layers (top and bottom) are described herein.

Various other embodiments are also presented on how the contact lens with sensor may have different sensors for detecting and measuring different aspects of the eye. Some embodiments measure IOP, some measure temperature changes, and still other embodiments measure the strain the eye may exert on the contact lens. Various devices may be used to collect the data from the sensors, and these devices include mobile phones, tablets, computers, and optical sensors. The optical information may be used in a program or app to provide a readily understandable and/or usable summary of the data collected to a user, health care provider, or other party.

Figure 1:
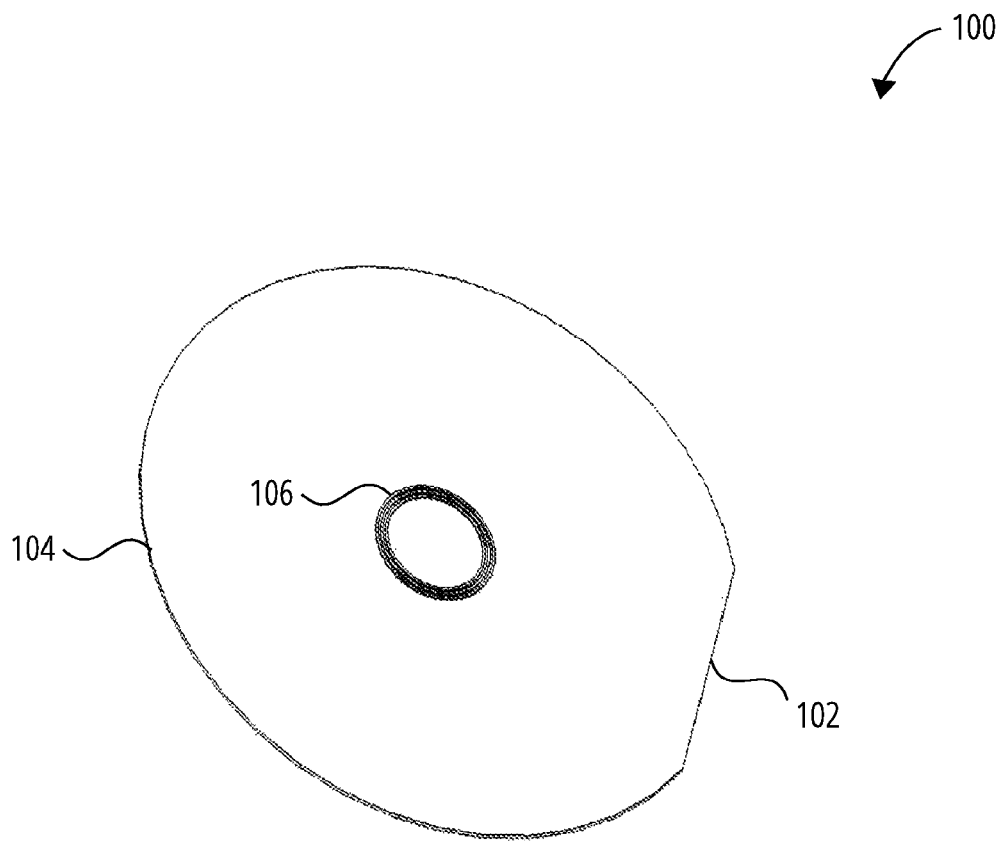
FIG. 1 illustrates an planar substrate in accordance with an embodiment 100.
Figure 2:
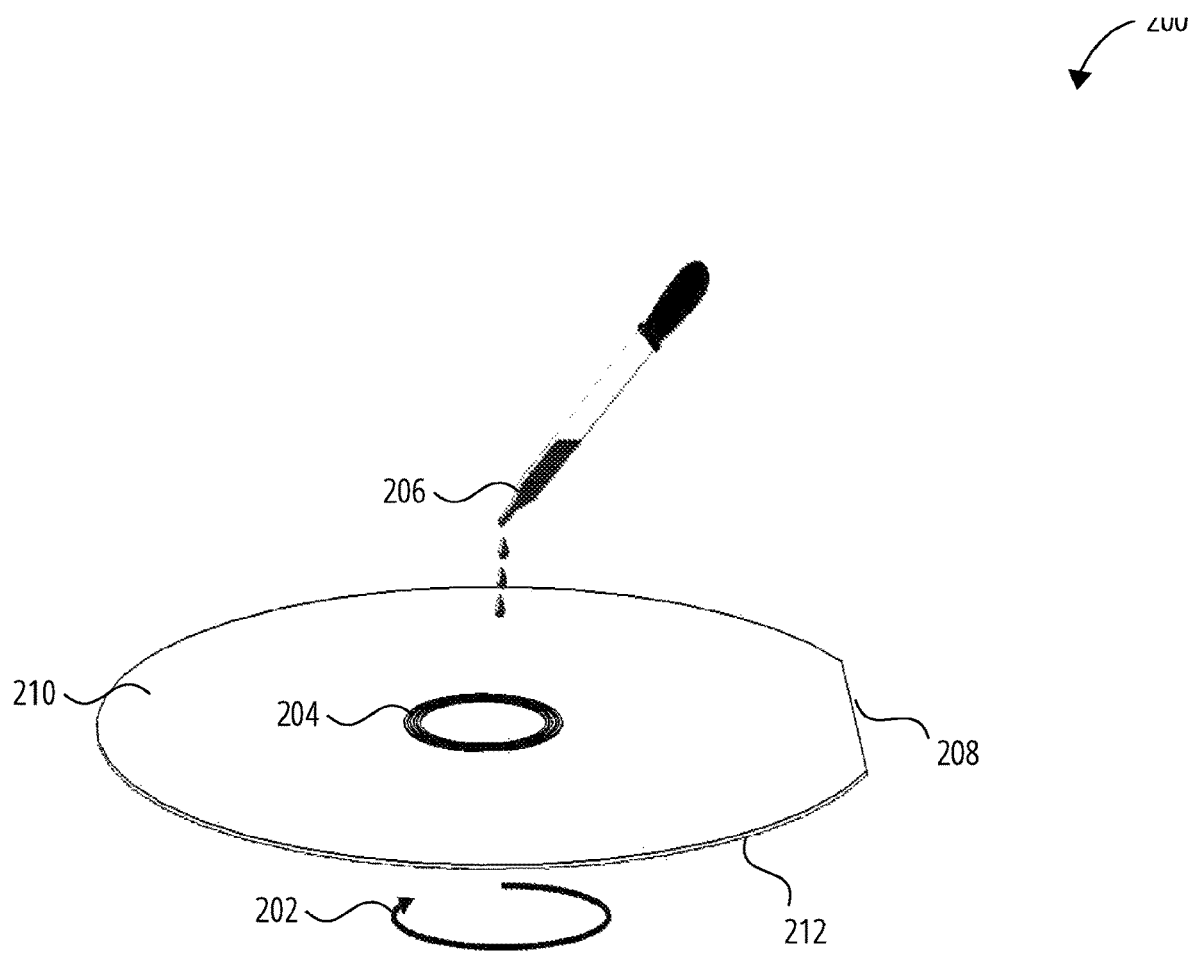
FIG. 2 illustrates an application of an elastomeric material to a mold according to an embodiment 200.
Figure 3:
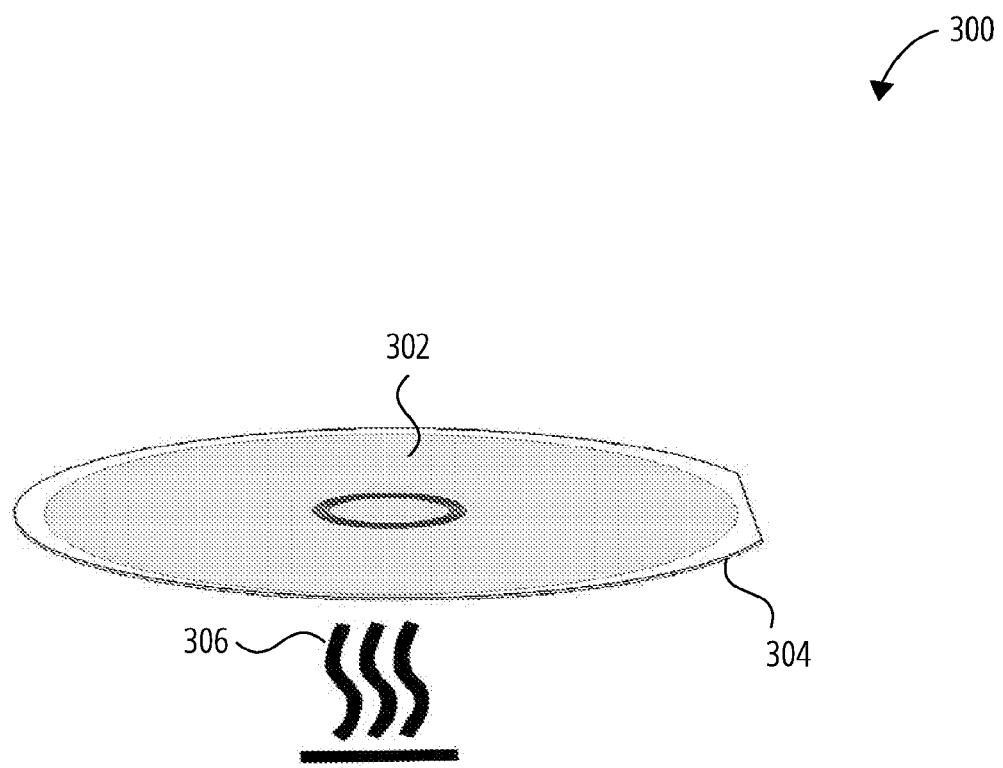
FIG. 3 illustrates curing a material in accordance with an embodiment 300.
Figure 4:
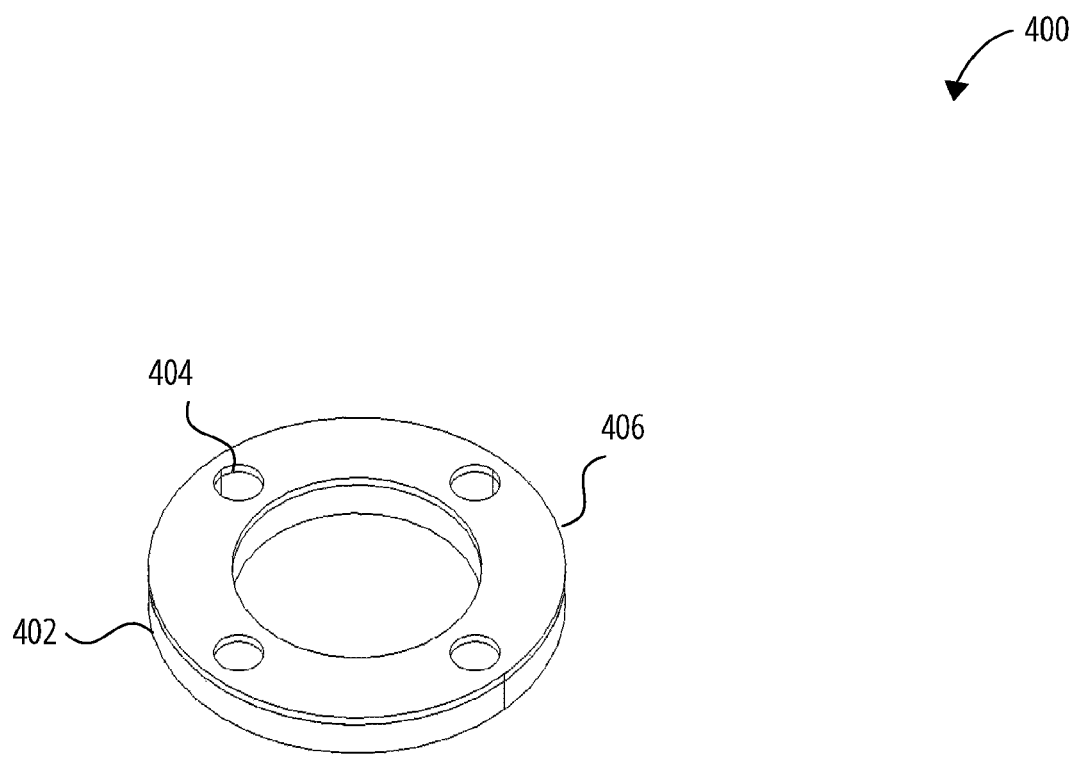
FIG. 4 illustrates a holder in accordance with an embodiment 400.
Figure 5:
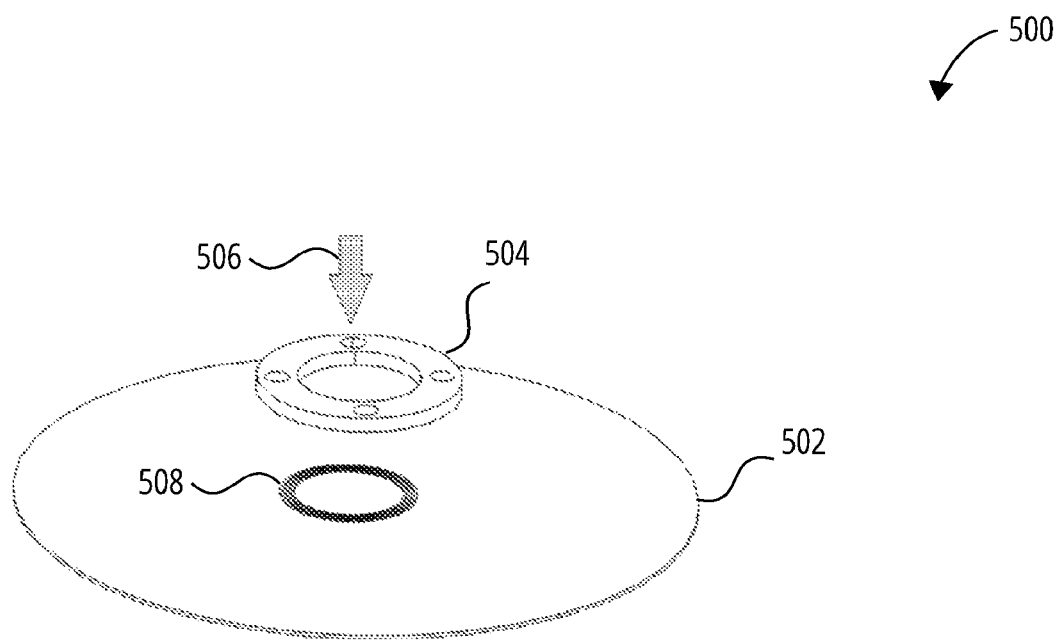
FIG. 5 illustrates placing a holder on a membrane in accordance with an embodiment 500.
Figure 6:
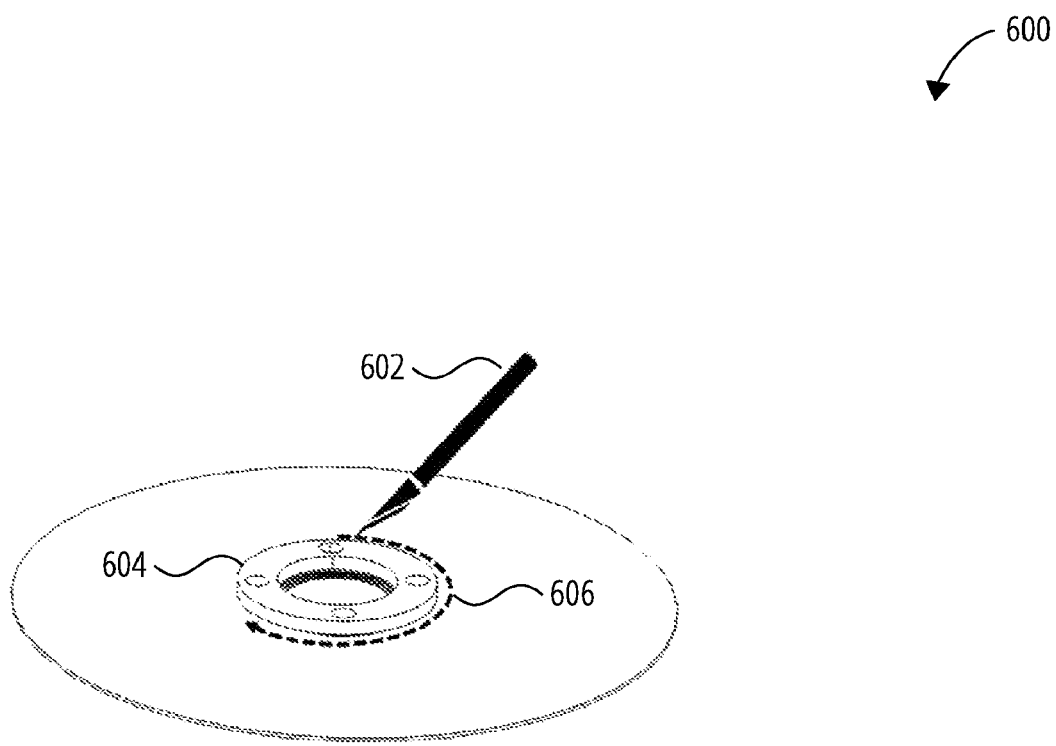
FIG. 6 illustrates excising a membrane template in accordance with an embodiment 600.
Figure 7:
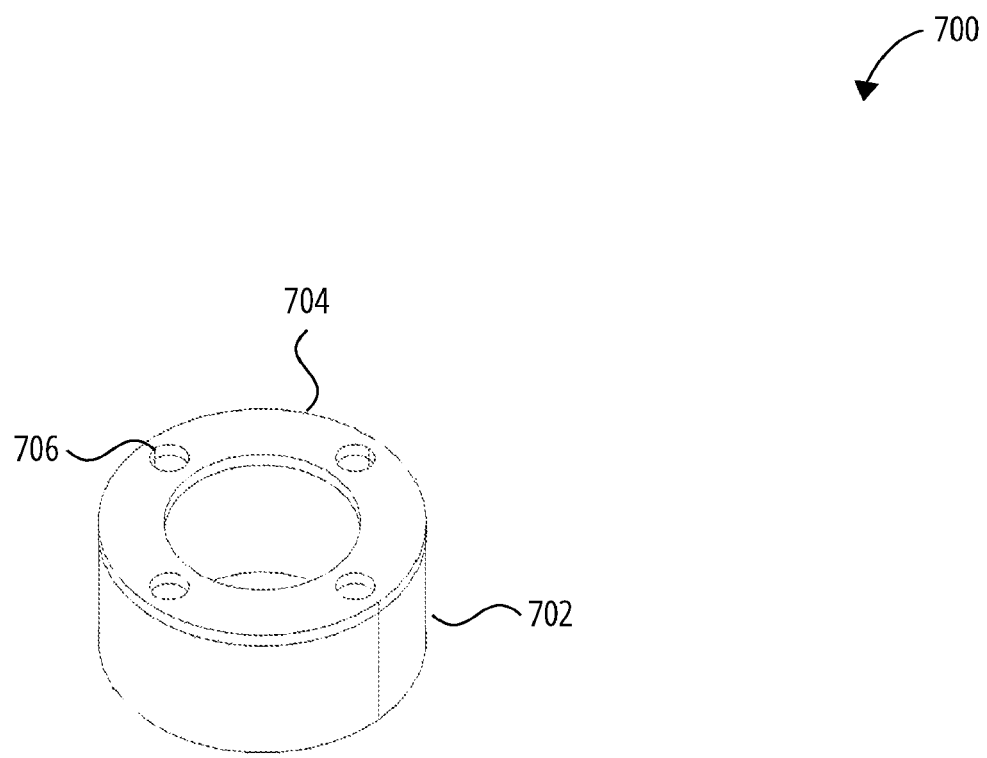
FIG. 7 illustrates a base assembly in accordance with an embodiment 700.
Figure 8:
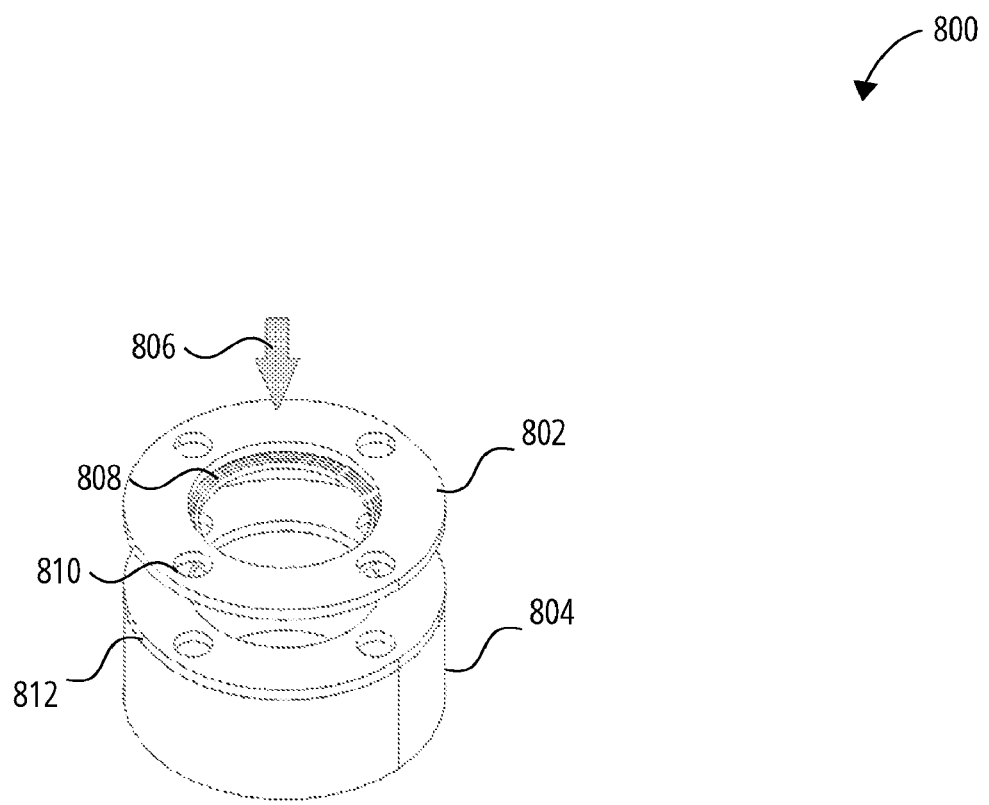
FIG. 8 illustrates an assembly of a holder and a base assembly in accordance with an embodiment 800.

In an embodiment, there may be a planar substrate, such as a silicon wafer, a metal plate or a polymer sheet, as shown in FIG. 1. The planar substrate 100 may have a relief pattern 106 or negative mold suitable to create or form a microfluidic structure in the material used on the mold. The planar substrate 100 may have a planar mold 104 and a relief pattern 106. The planar substrate may also have one or more flat edge 102 portions to facilitate use, handling or separation of the planar mold 104 from a material used with the planar mold 104.

In an embodiment, more than one mold may be present on the planar substrate. Although a single mold is shown, it should be understood that any number of molds may be made simultaneously on the same substrate.

A process is now described for making a mold that may be used for fabricating a contact lens with an intraocular pressure sensor. The process involves generally placing a liquid material on to a planar mold. The liquid generally being a substance that can be deposited in liquid form, then changed somehow to be generally solid. As the material solidifies, it assumes the texture and form of the planar mold. The material may solidify into a membrane. A holder may be placed on the membrane, and a portion of the membrane may be excised around the holder. The holder may have a sticky or tacky surface so the excised portion of the membrane will adhere to the holder as the holder is moved. The holder may then be fastened to a base assembly with the membrane section between the holder and the base assembly. The fastening of the holder to the base assembly may allow the membrane to transfer onto the base assembly. The base assembly may then be pressed onto a curved mold in a manner that causes the membrane template to be stretched over the curved mold. The base assembly may have an aperture or fill port, allowing the back end of the base assembly to be filled with a material that will bind to the membrane template as it is stretched over the curved mold. The added material may then be cured so it solidifies. When the process is completed, the curved mold may be separated from the membrane template.

The various stages of the process for making the curved mold are now described and illustrated in more detail. In an embodiment, there may be a planar substrate 212 having a planar mold 210 on one or both sides. The planar mold 210 may have a relief pattern 204. A polymer or elastomeric material 206 may be deposited on the planar mold 210. The planar mold 210 may be stationary or in rotation 202 while the material 206 is added to the planar mold 210. The material 206 thickness may be controlled while rotation 202 of the planar mold 210 is underway. The speed of rotation may be controlled to choose an appropriate thickness of the material 206 as is well understood in the art.

In various embodiments the planar substrate 212 may be rotated on a spindle or a platter or any other mechanism as is well understood in the art. The material may be added in a drop wise fashion or streamed onto the planar mold 210. The method of adding the material 206 to the planar mold 210 may depend on the type of material, and the ability to control its deposition on the mold, or the adjustment of the material thickness while under rotation.

Once the material is distributed on the planar mold 304, it may be cured using energy 306, such as UV light, heat, or other forms of energy as are well understood in the art. The curing time may be done according to the manufacturing recommended time, or it may be less or more. The material when cured forms a substantially solid form. By substantially solid, applicant means the material may have regions of the cured material that may retain some fluidic properties. In some embodiments, the material may be partially cured. In an alternative embodiment, the material may be a substance that may be converted back into a liquid state, semi-liquid state or vapor state with the application of energy or chemical reagents. In some embodiments, the material may be an elastomeric compound.

In some embodiments, the thickness of the membrane sheet 302 may vary between 1 to 999 microns (μm). In some embodiments the thickness of the membrane sheet 302 may vary between 25 to 600 microns. In still other embodiments, the membrane sheet 302 thickness may range from 50 to 500 microns.

Once the membrane material is cured, a holder 402 may be placed on the membrane sheet. The holder may be circular or an annular ring. In some embodiments the footprint of the holder may be sized to be a specific diameter larger than the diameter of the microfluidic channels formed in the membrane sheet. In other embodiments the holder footprint may be sized to match the external diameter of the microfluidic channels. In some embodiments, where the shape of the microfluidics channels may not be regular, or not substantially circular, the holder may have a corresponding footprint of equal or larger size. In some embodiments where the holder may be an annular ring, the inner diameter of the annular ring may be sized such that the inner diameter exceeds the diameter of the microfluidics channels of the membrane sheet.

In various embodiments, the holder 402 may have one or more holes 404. The holes may be used to align holes of other parts for fastening the holder to another part to create an assembly. In some embodiments the holder may have an adhesive layer 406. In an embodiment, the adhesive layer 406 may be double sided tape. In some embodiments the adhesive layer 406 may be a tacky material affixed to the holder 402. In still other embodiments, the adhesive layer 406 may be a mechanical gripper, suction device or other temporary mechanical fastener.

The process of making the curved mold may now proceed to centering the holder 504 on to the membrane sheet 502. The tacky portion (not shown) of the holder 504 faces the membrane sheet 502 so the tacky portion may be in direct physical contact with the membrane sheet 502. The holder 504 may be pressed on to the membrane sheet 502 following the placement direction 506 as shown. The aperture of the holder may be place around or on the microfluidic channels 508.

Once the holder is properly in place, the membrane template may be excised from the membrane sheet. An excise tool 602 may be used to create an excise path 606 around the holder 604.

In various embodiments, the excise tool 602 may be a knife, a laser, or any cutting tool or device (such as an energy device) that may be used to sever the membrane template from the membrane sheet. The excise tool 602 may follow a preprogrammed path, such as that created by a computer controlled cutting tool, or it may be a mechanical device on a cam following shaft. The membrane template may be cut manually as well.

In some embodiments, the planar mold or planar substrate may be excised when the membrane is excised. In alternative embodiments, the excise path does not damage the planar mold or substrate. In those embodiments where the planar mold is undamaged, it may be reused.

In an embodiment, there may be a base assembly 702. The base assembly 702 may have one or more holes 706 in a pattern to match the holes of the holder, so that a fastener such as a screw may be used to fasten the holder to the base assembly 702. The base assembly 702 may have a tacky or adhesive layer 704. The adhesive layer may be similar to those previously described. The base assembly 702 may have an aperture such that it is shaped like a tube or hollow cylinder.

The holder 802 with the membrane template 808 facing the base assembly 804, may now be assembled. The holder 802 and base assembly 804 may be put together via connection 806 force, with the various holes 810 aligned. The holes 810 may then receive fasteners such as screws, pegs, or glue. An adhesive 812 may be placed on the connection side of the base assembly 804 so the membrane template 808 may adhere to the base assembly 804 when the holder is separated from the combined base assembly 702

The membrane template 808 may be a uniform thickness with an aperture in the middle (inside the area defined by the microfluidics channels. In an alternative embodiment the membrane template is contiguous (having no aperture). In an embodiment, an annular ring of material may be used to create a sensor region that may be attached to a pre-existing contact lens.

In some embodiments, the microfluidic channels may be oriented to face a particular direction. In other embodiments, other fixtures may have their orientation matched to the combined holder and base assembly.

Figure 9:
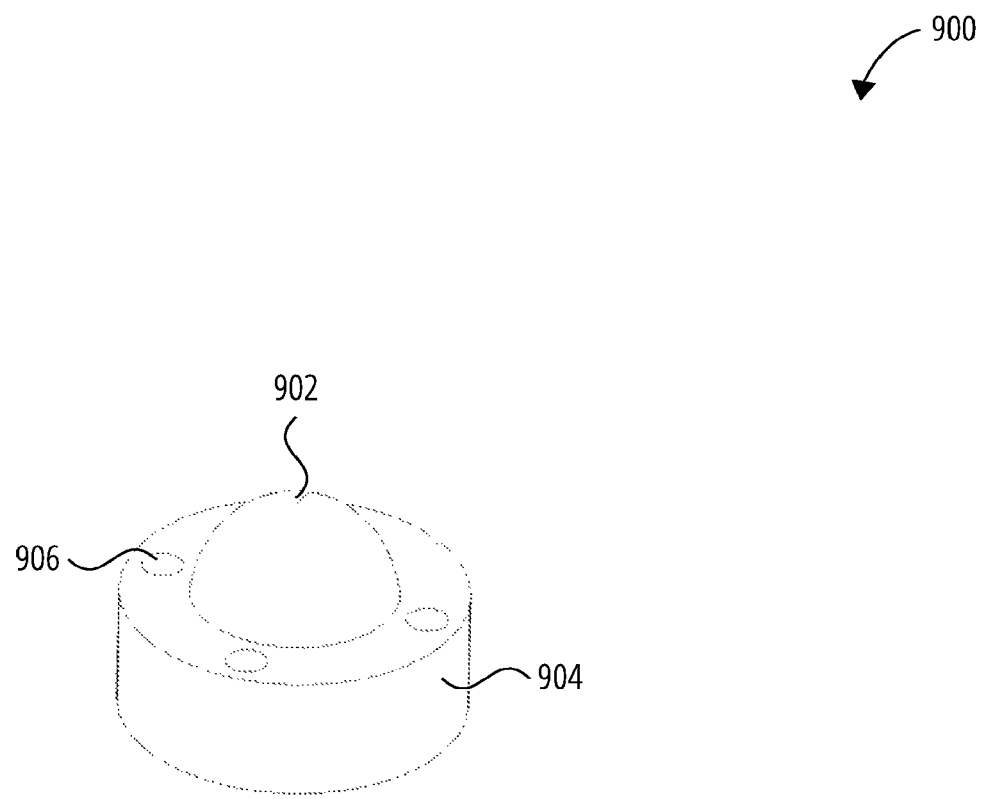
FIG. 9 illustrates a curved mold in accordance with an embodiment 900.

In various embodiments, the base assembly may be combined with a lower base assembly 904 as shown in FIG. 9. The lower base assembly 904 may have a curved mold 902. The curved mold 902 may be a hemisphere or sphere shaped mold, a partially curved mold of a particular radius and arch length or arch circumference. In some embodiments the curved mold 902 may be continuous in curvature to the seam between the curved mold 902 and the lower base assembly 904.

In various embodiments, the lower base assembly 904 may also have one or more fixture holes 906. The fixture holes 906 may have the same shape an orientation as the holes in the base assembly, allowing the lower base assembly 904 and the base assembly to be fastened to each other using screws, pegs or other fasteners. While screws are envisioned as a possible embodiment, the various assembled portions (holder and base assembly, base assembly and lower base assembly) may be fastened using clamps, glue, clips or other mechanisms. The assembled portions may have an interference fit with one another, or a mechanical engagement such as one screwing on to the other.

In various embodiments, the curved mold 902 may be made of glass, a non-stick material, or other surface that may cause the membrane template to stretch over the curved mold and assume substantially the same radius of curvature of the curved mold, without distorting the membrane template or the microfluidic channels to the point that either element cannot function.

Figure 10:
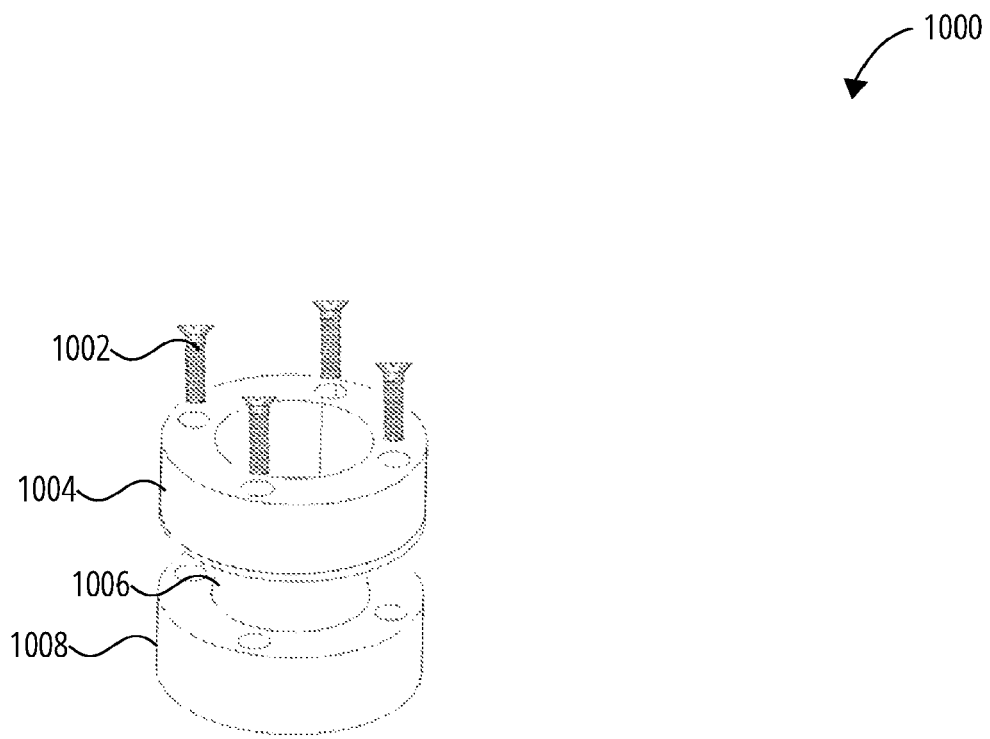
FIG. 10 illustrates an assembly of a curved mold and base assembly according to an embodiment 1000.

As previously described, various embodiments may assemble the base assembly with the lower base assembly as shown in FIG. 10. In an embodiment, screws 1002 may be used as fasteners to secure the base assembly 1004 and lower base assembly 1008. The base assembly 1004 may be in an orientation such that the membrane template faces the curved mold 1006 during assembly, so that the membrane template makes contact with the curved mold 1006, and is stretched over the curved mold 1006 as the base and lower base assemblies are fastened together.

In some embodiments, the membrane template may not be completely solidified or cured, so as to allow the membrane template to take the shape over the curved mold 1006 better.

Figure 11:
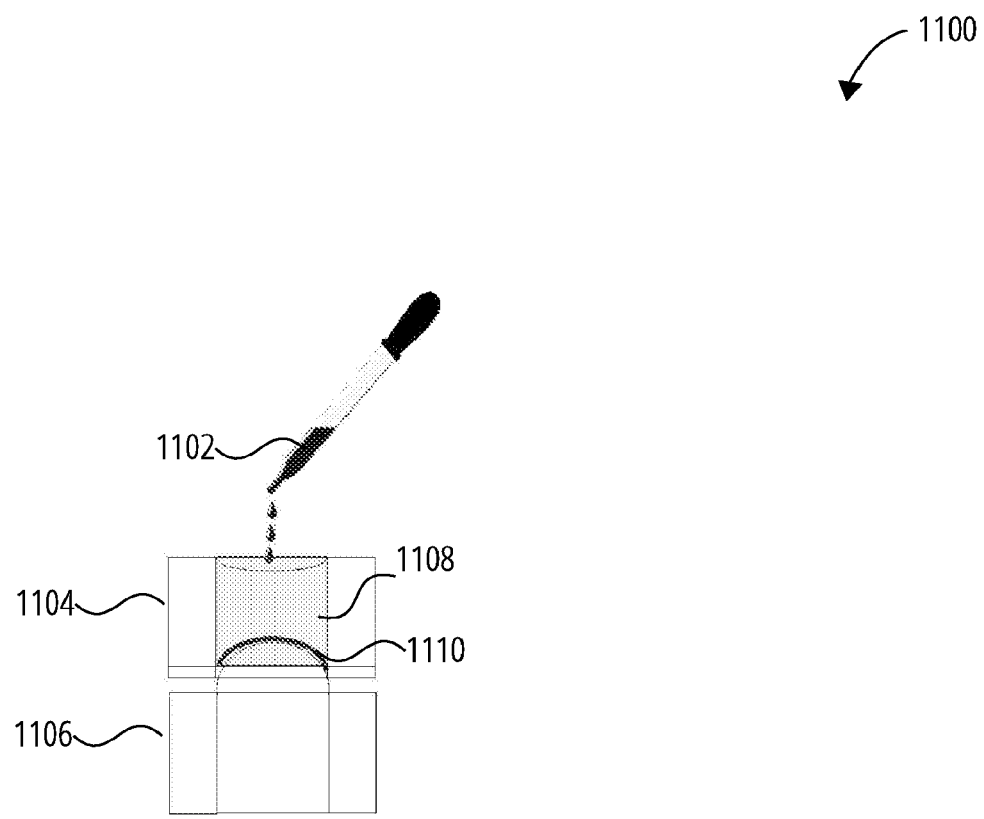
FIG. 11 illustrates backfilling a membrane in a base assembly in accordance with an embodiment 1100.

In an embodiment, the base assembly may have a cavity 1108 or an aperture behind the membrane template 1110 as shown in FIG. 11. In an embodiment, the cavity 1108 may be back filled with additional material 1102 to partially or completely fill the cavity 1108 of the base assembly 1104. The membrane template 1110 acts as a barrier, preventing the back filled material from contacting the lower base assembly 1106.

In an embodiment, a curing agent elastomeric material such as polydimethylsiloxane (or PDMS) may be applied on to the back surface of the membrane template 1110. The elastomeric material may then be drained. Once the elastomeric material has been drained, the backside cavity 1108 may be filled with a premixed elastomeric material or equivalent material. A curing agent may improve the binding of the elastomeric material layer after curing.

Figure 12:
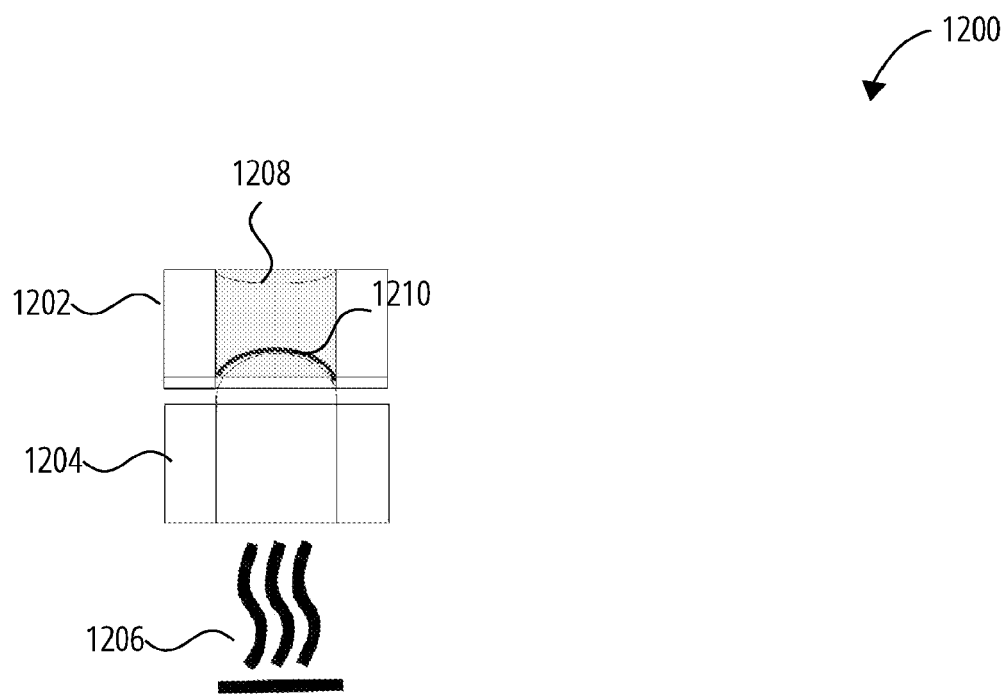
FIG. 12 illustrates curing the material of the backfill in accordance with an embodiment 1200.

After material has been added into the cavity of the base assembly, it may be cured as shown in FIG. 12. The base assembly 1202 and the lower base assembly 1204 may remain fastened while energy 1206 may be applied to the newly poured mold 1208 of material behind the membrane template 1210. The energy may be any kind suitable to cure the material in the cavity of the base assembly 1202. Some non-limiting examples include ultraviolet (UV) light, heat, visible and non-visible light energy, or other materials, such as a chemical curing agent. The assembled base and lower base combination may be placed in a chamber, such as an oven or light chamber, for the curing process. While in an embodiment, the energy 1206 is shown radiating from a single direction, it should be understood that the energy may originate from one or more point sources, or may originate from an energy source, and indirectly reach the mold 1208 to cure it, as in the case of an oven chamber.

Figure 13:
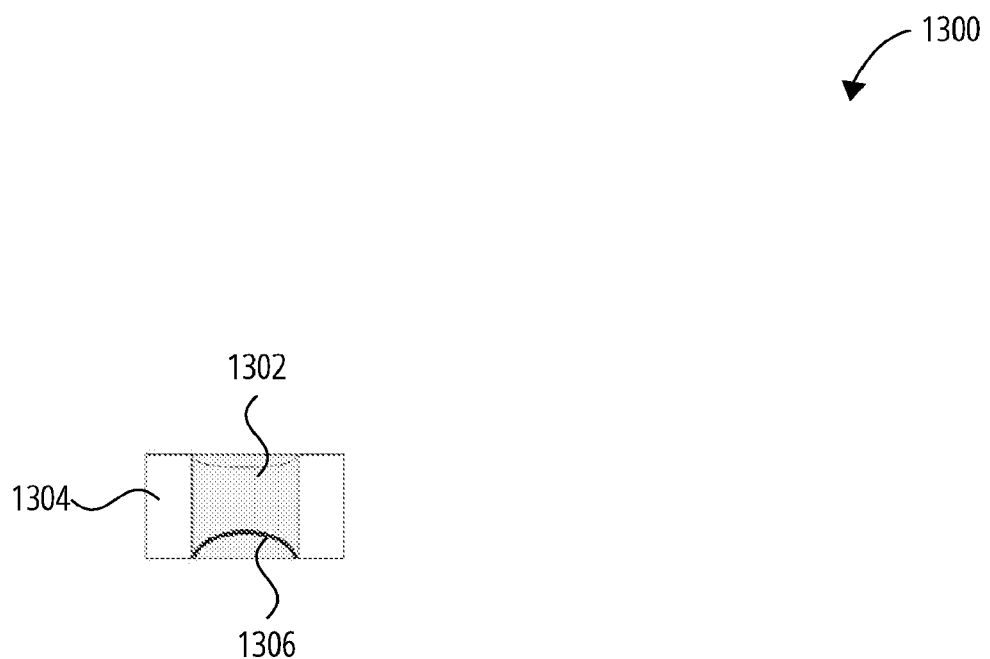
FIG. 13 illustrates a completed mold in accordance with an embodiment 1300.

A cross section of the mold 1302 formed in the base assembly 1304 and the membrane template 1306 are shown in FIG. 13. The mold 1302 may be separate from the lower base assembly, and may be used in the imprinting process for making contact lens and IOP sensing devices.

An alternative method of making a contact lens and IOP sensor mold is now described. In various embodiments, there may be a curved mold that may be coated with a photoresist. The photoresist may then be cured for a period of time. The cure time may be more, less or equal to the amount of time normally used for a photoresist material. When the photoresist has reached a suitable cure state, a pattern may be created in the surface of the photoresist, and the pattern may be developed to produce one or more reliefs or other features for the creation of microfluidic channels. An elastomeric compound may then be poured over the patterned surface and cured to produce a contact lens and IOP sensor mold.

Figure 14:
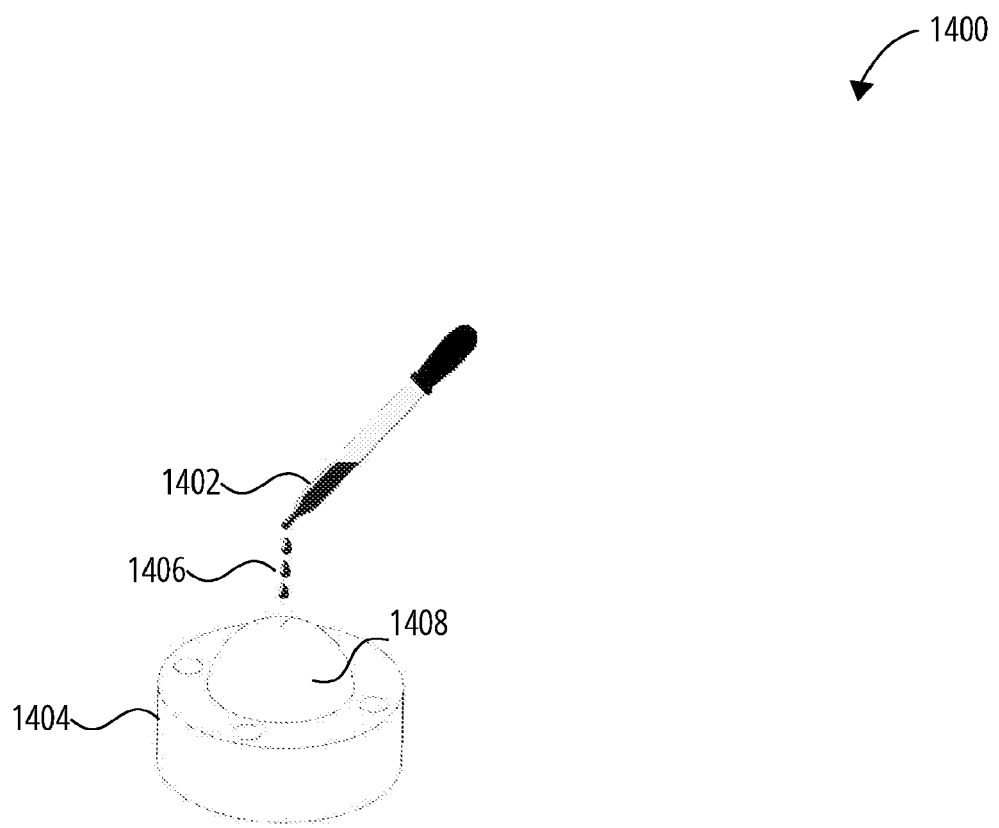
FIG. 14 illustrates creating a membrane on a curved mold in accordance with an embodiment 1400.
Figure 15:
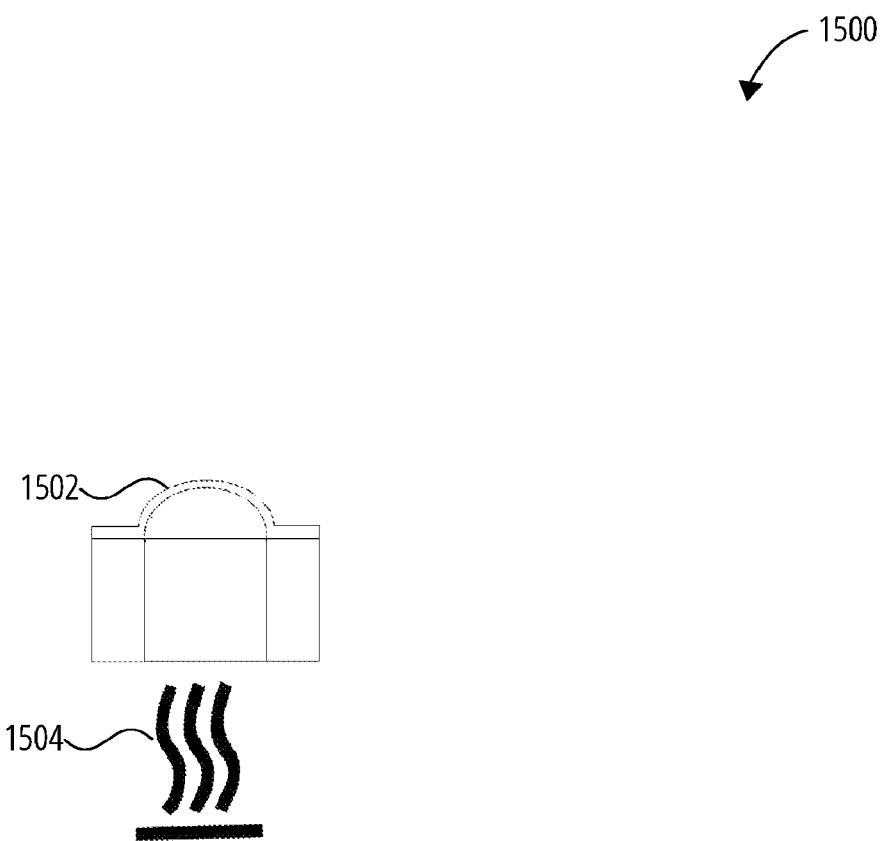
FIG. 15 illustrates curing the membrane on the curved mold in accordance with an embodiment 1500.
Figure 16:
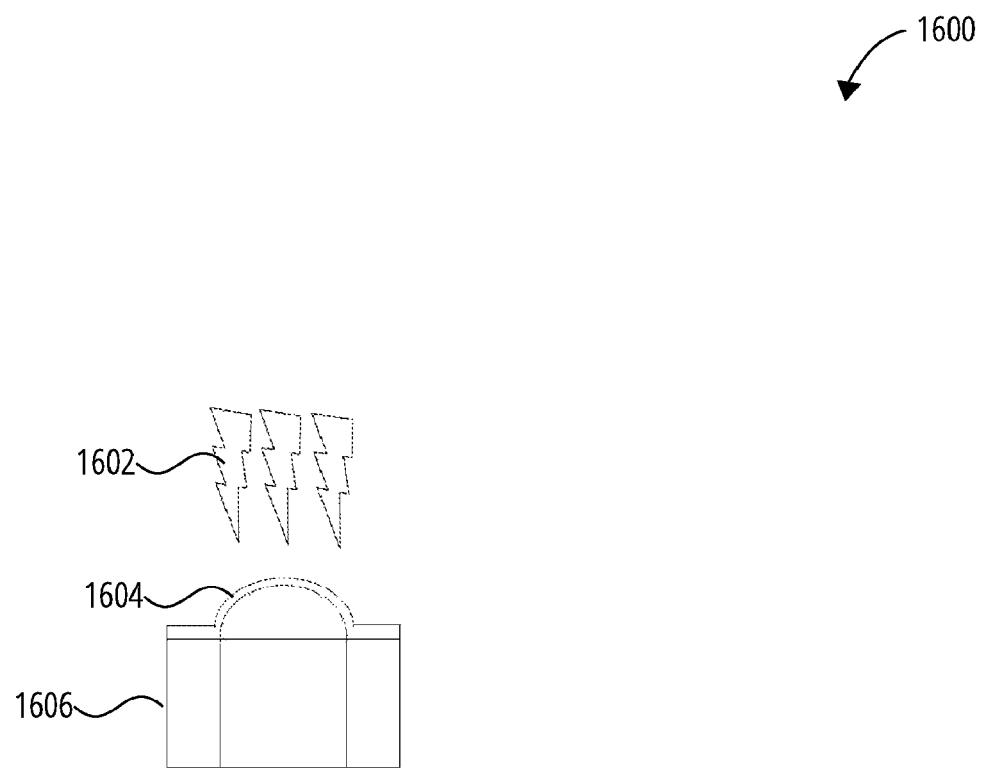
FIG. 16 illustrates an energy treatment of a membrane according to an embodiment 1600.

In an embodiment, a bottom membrane layer may be fabricated by drop casting 1406 a thin layer of an elastomeric material 1402 (such as premixed PDMS) onto a curved mold 1408 as shown in FIG. 14. The curved mold 1408 may sit or be affixed to a lower base assembly 1404. The curved mold may be a glass hemisphere, sphere or other suitable material. The elastomeric material may be a photoresist material.

In an embodiment, the Elastomeric membrane 1502 may be cured by the application of energy 1504. In various embodiments, the energy 1504 may be thermal energy (heat), UV light, or other curing energies. In some alternative embodiments, the Elastomeric membrane 1502 may be cured by exposing it to a curing compound. The elastomeric membrane 1502 thickness may be controlled by the composition of the material used for the membrane, the viscosity or a spinning process prior to curing.

In an embodiment, the elastomeric layer may be treated with plasma 1602 to improve bonding of subsequent UV curable polymer layers. The lower base assembly 1606 with the curved mold serves as the substrate for the membrane and photoresist layer 1604 during plasma 1602 treatment. The plasma 1602 may be used to create a pattern in the photoresist.

Figure 17:
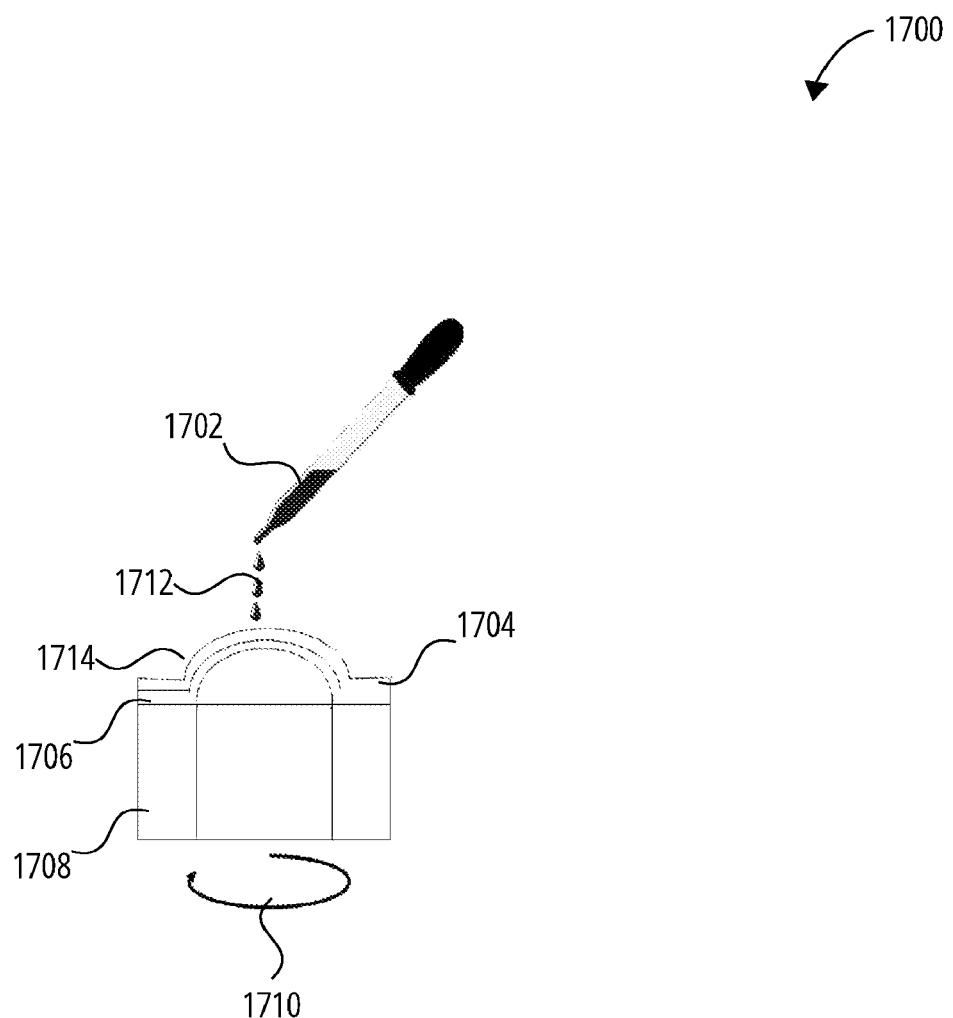
FIG. 17 illustrates drop casting a membrane according to an embodiment 1700.
Figure 18:
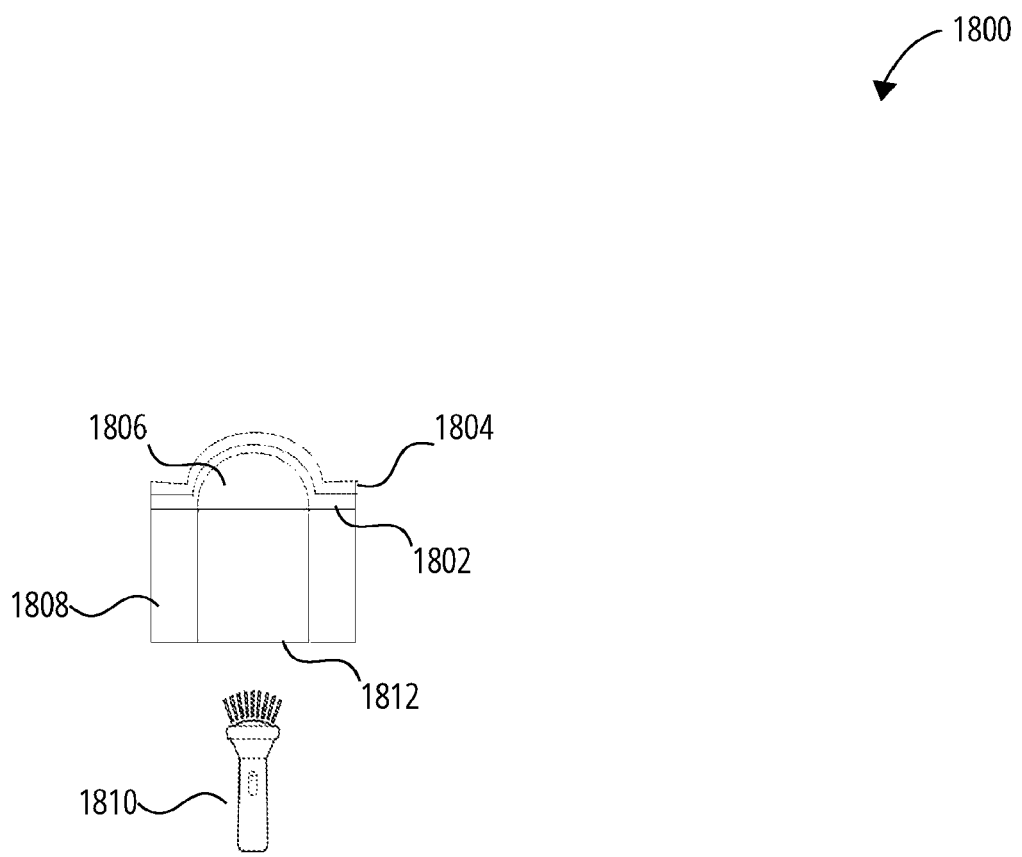
FIG. 18 illustrates curing a membrane according to an embodiment 1800.

In an embodiment, an elastomeric compound 1702 may be drop cast 1712 to form a PDMS membrane 1714 (or other suitable material) as shown in FIG. 17. The PDMS may be drop cast 1712 on a curable polymer layer 1704 with another membrane 1706 layer underneath. The lower base assembly 1708 may be rotated in either direction as the curable elastomeric compound 1702 is spin coated 1710 on the curable polymer layer 1704.

In some embodiments, the PDMS membrane 1714 may be between 0.01 microns and 999 microns. In some embodiments, the PDMS membrane 1714 may be between 1 and 300 microns. In still other embodiments the membrane may be between 10-50 microns.

In an embodiment, a curable polymer layer 1804 may be cured using UV light 1810 projected through an aperture 1812 of the lower base assembly 1808. The UV light 1810 may shine through a membrane 1802 and a curved mold 1806 (which may be partially or mostly transparent to the UV light). When the curing process is completed, the mold may be finished.

Figure 19:
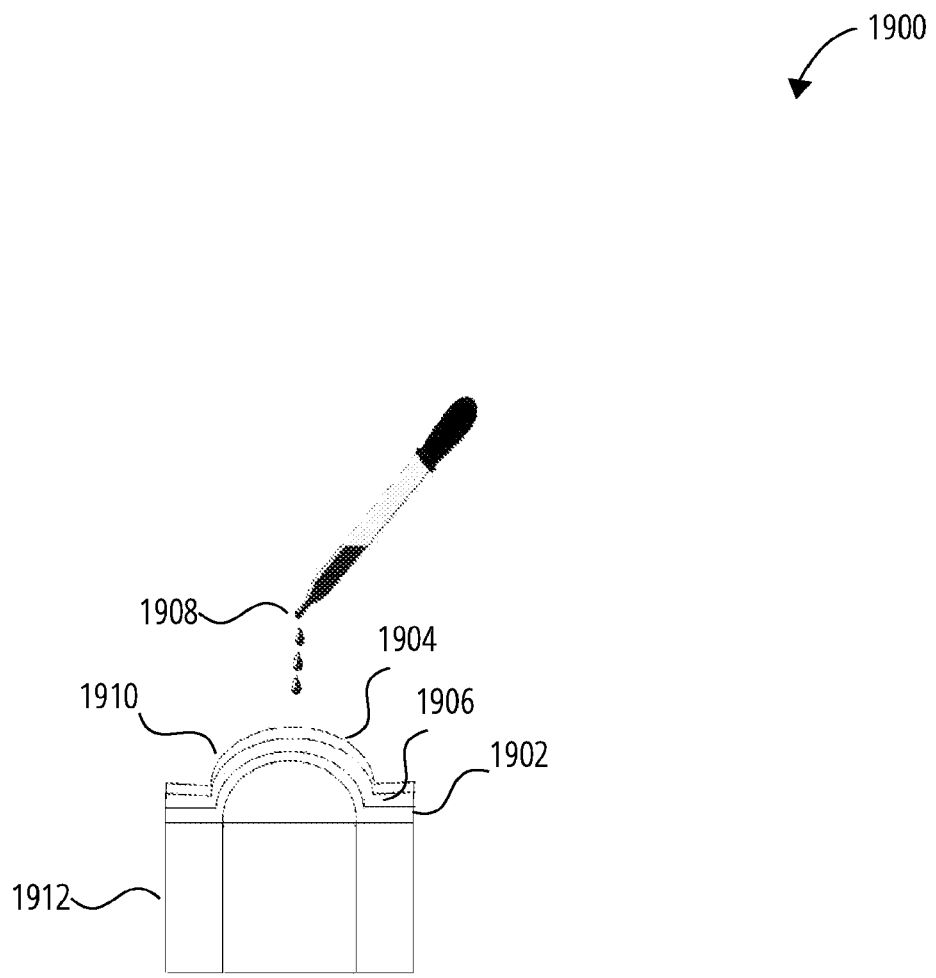
FIG. 19 illustrates a step in a method of making a lens and sensor device according to an embodiment 1900.

In an embodiment, there may be a thin bottom PDMS membrane 1910 with a partially cured UV curable polymer layer 1906 which may be drop cast 1908 by applicator to form a second layer 1904 of a UV curable polymer as shown in FIG. 19. In an embodiment, the membrane 1910 may have a base elastomer 1902 layer, a first UV curable polymer layer 1906 and a second layer 1904 of UV curable polymer. The membrane 1910 may be formed on a curved mold supported by a base assembly 1912.

Figure 20:
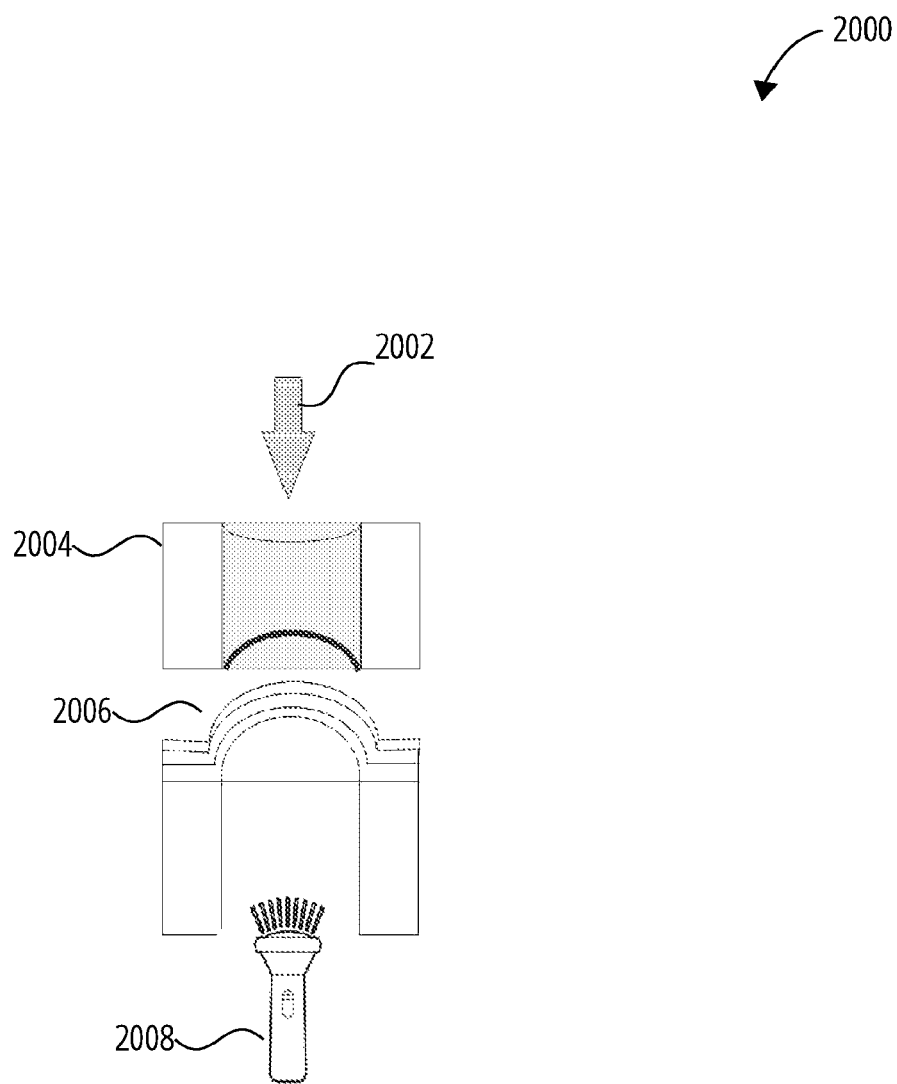
FIG. 20 illustrates a step in a method of making a lens and sensor device according to an embodiment 2000.

In an embodiment a curved mold 2004 may be brought into contact with an assembly previously described and a controlled pressure 2002 may be applied to perform the imprinting step as shown in FIG. 20. The layer 2006 may be cured partially by UV light 2008, while the two components are in contact.

Figure 21:
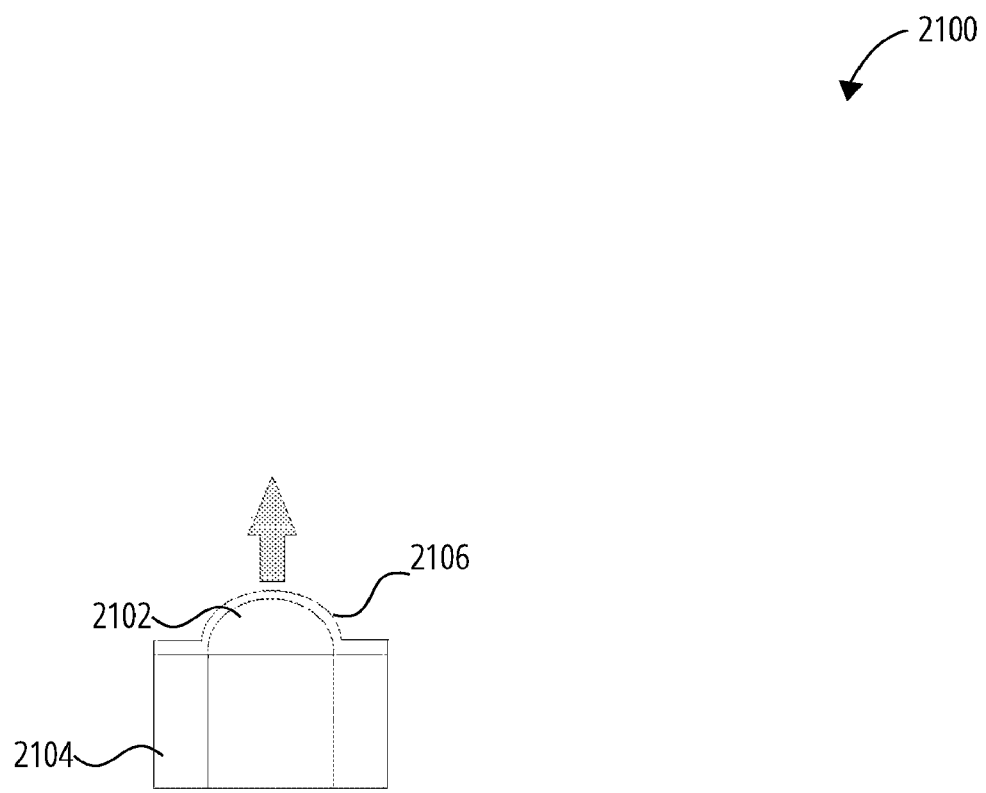
FIG. 21 illustrates a step in a method of making a lens and sensor device according to an embodiment 2100.

In an embodiment, a PDMS patternless membrane 2106, prepared as previously described, may be peeled from the curved mold 2102 which may be supported by a base assembly 2104 as shown in FIG. 21.

Figure 22:
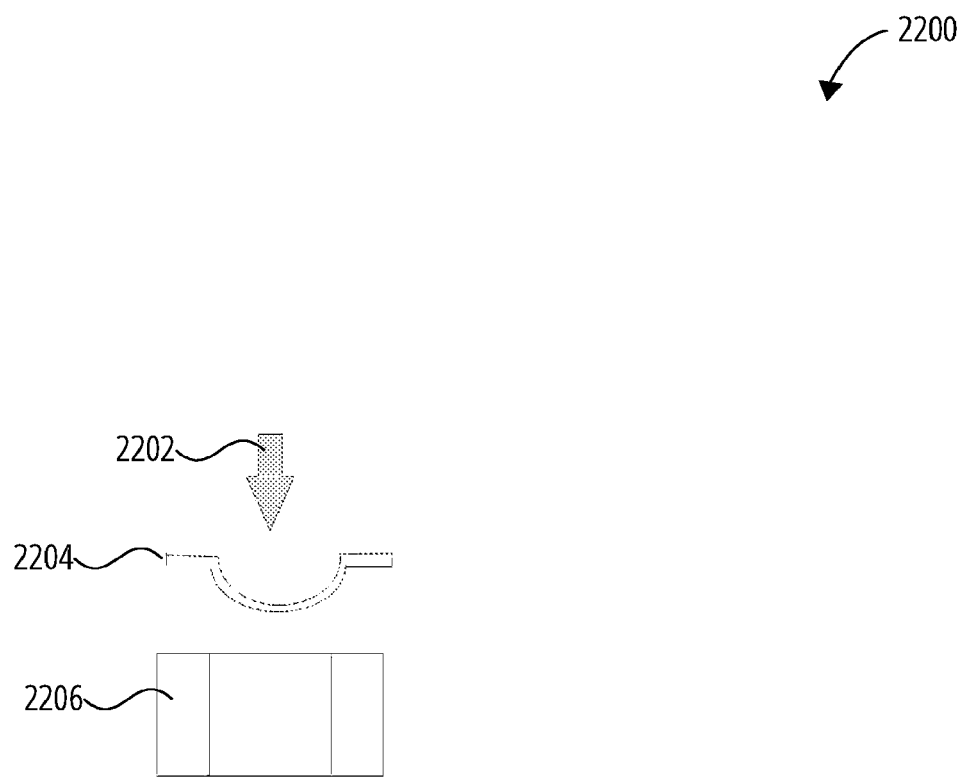
FIG. 22 illustrates a step in a method of making a lens and sensor device according to an embodiment 2200.

In an embodiment, a PDMS membrane 2204 may be flipped upside down and placed on a cylindrical holder 2206 as shown in FIG. 22. The upside-down membrane 2204 may be pressed into the holder 2206 using suitable force 2202.

Figure 23:
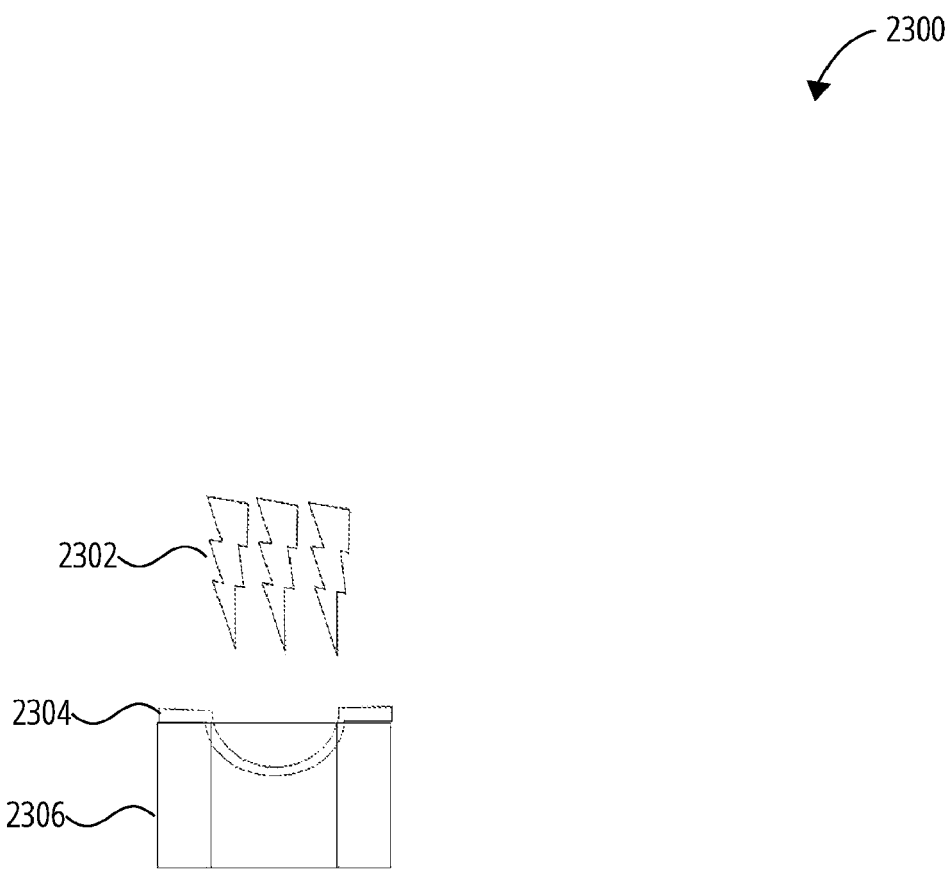
FIG. 23 illustrates a step in a method of making a lens and sensor device according to an embodiment 2300.

In an embodiment, the concave side the PDMS membrane 2304 may be exposed to plasma 2302 to promote adhesion of UV curable polymer layers as shown in FIG. 23. The membrane 2304 may be held in place by a membrane holder 2306.

Figure 24:
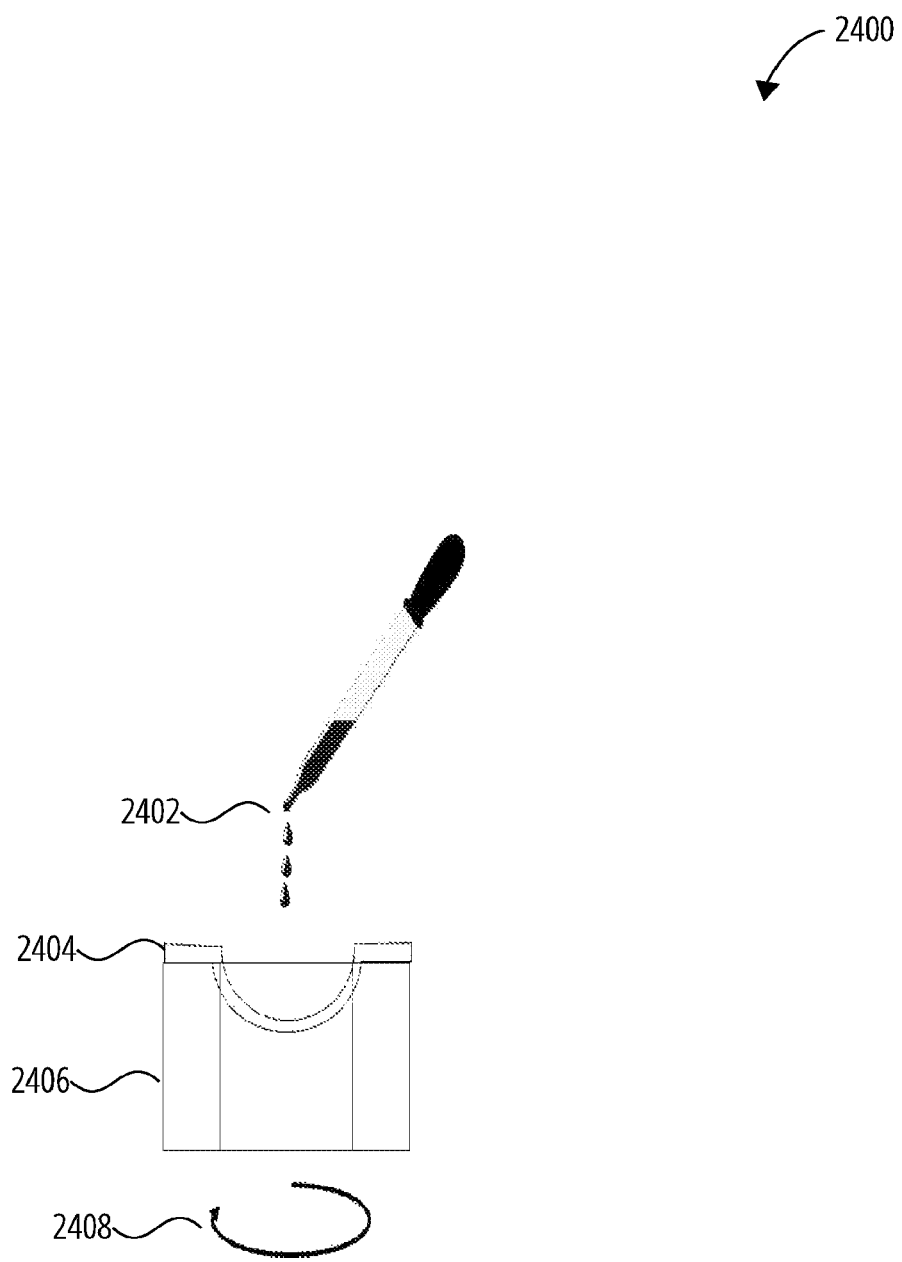
FIG. 24 illustrates a step in a method of making a lens and sensor device according to an embodiment 2400.

In an embodiment, an applicator may be used to drop cast a UV curable resin 2402 in to the concave side of the curved membrane 2304 as shown in FIG. 24. The membrane holder 2406 may be rotated 2408 to spin coat the resin on the membrane.

Figure 25:
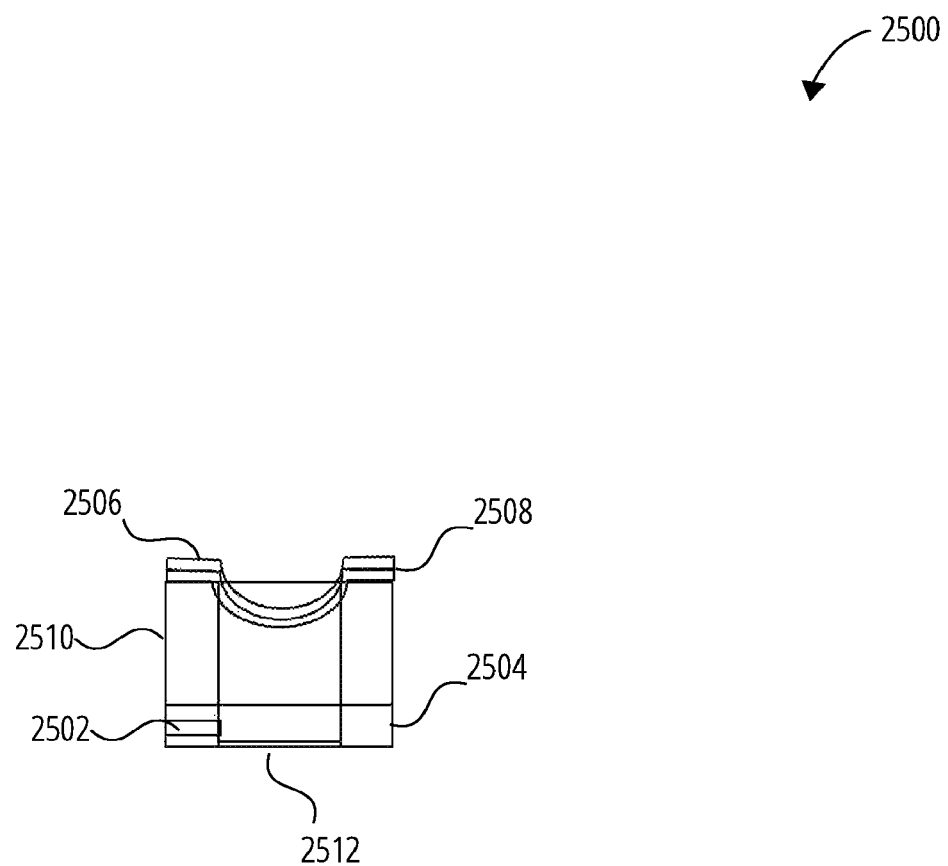
FIG. 25 illustrates a step in a method of making a lens and sensor device according to an embodiment 2500.

In an embodiment, there may be a pressure cap 2504, with a gas port 2502 and a window 2512 as shown in FIG. 25. The window 2512 may be transparent to UV light and/or other forms of optical energy. The membrane 2508 may be attached to a holder 2510. The membrane may have a partially cured UV curable resin layer 2506.

Figure 26:
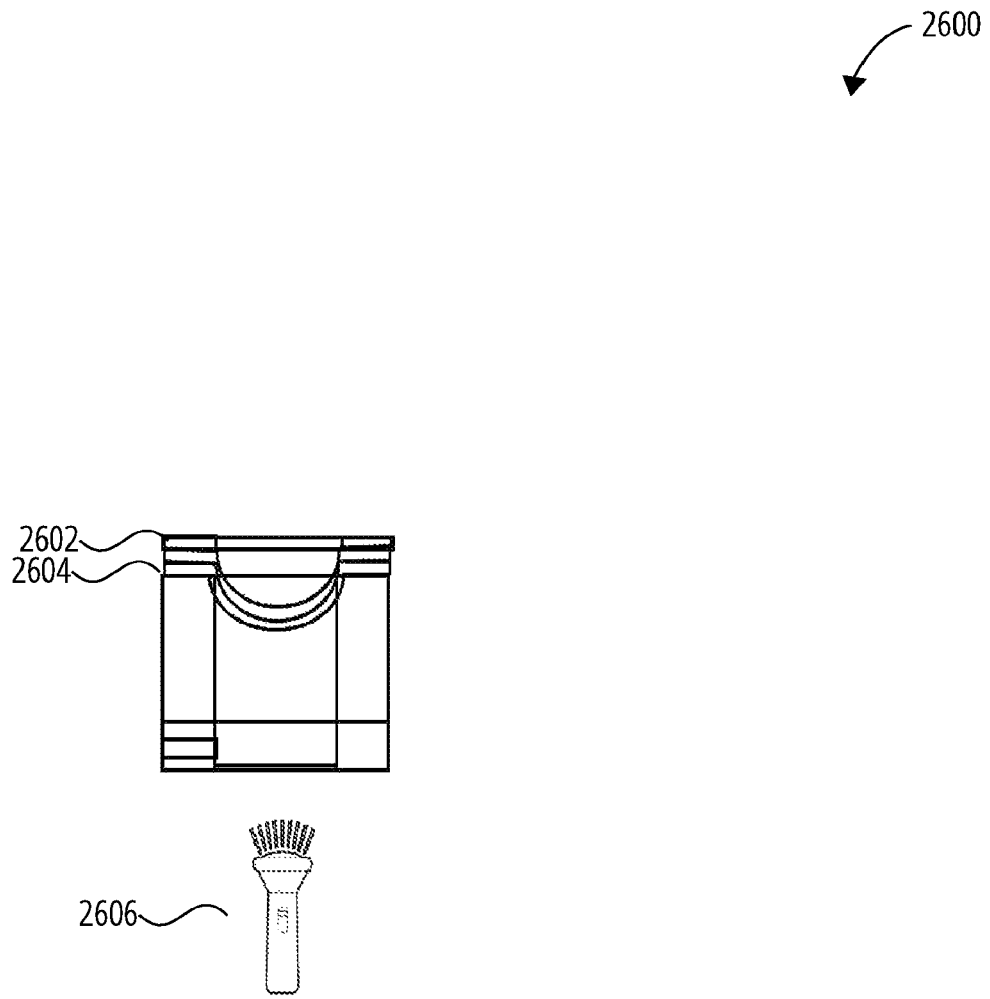
FIG. 26 illustrates a step in a method of making a lens and sensor device according to an embodiment 2600.

In an embodiment, a retaining ring 2602 may be attached from the top side of the assembly in FIG. 25 to hermetically seal the pressure chamber and hold the PDMS membrane 2604 in place as shown in FIG. 26. The retaining ring 2602 may hold the membrane 2604 in place generally without causing in plane strain that may cause deformation of the membrane. The UV curable resin may be lightly cured using the UV light 2606 to maintain partial adhesive properties.

Figure 27:
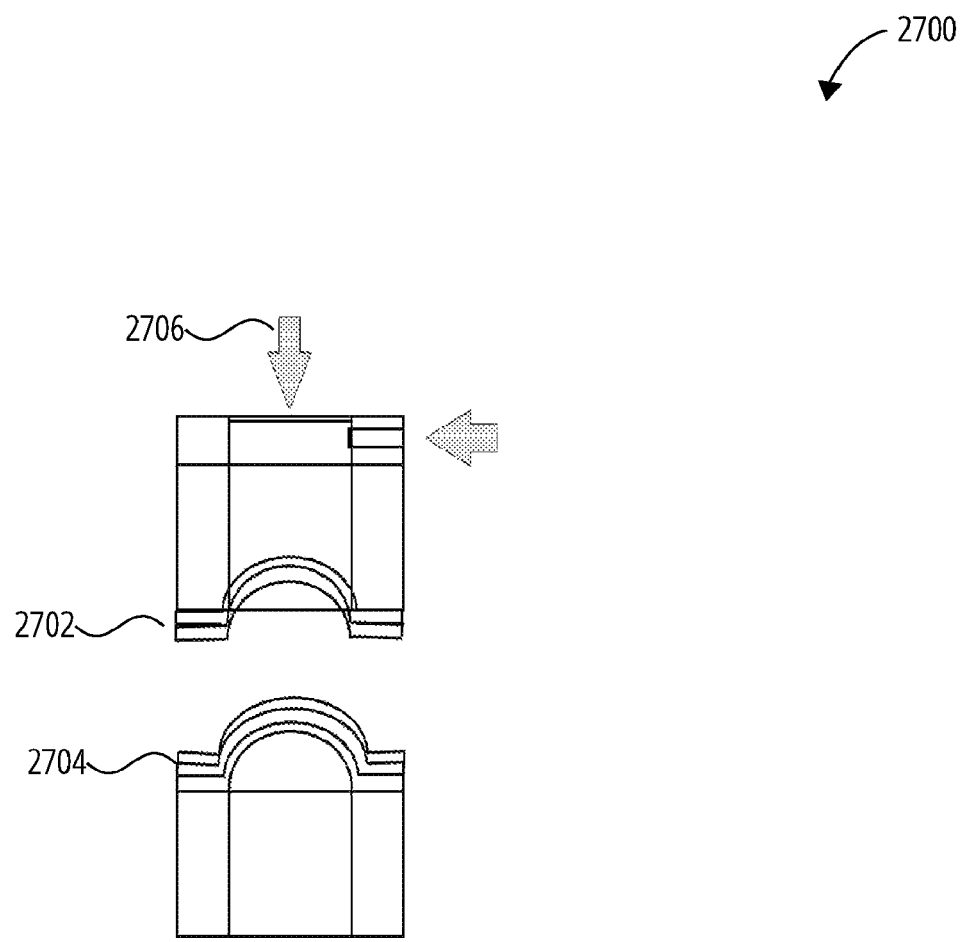
FIG. 27 illustrates a step in a method of making a lens and sensor device according to an embodiment 2700.

In an embodiment, the two assemblies of the device with the top membrane 2702 and the bottom membrane 2704 may be brought into contact with the application of pressure 2706, as shown in FIG. 27.

Figure 28:
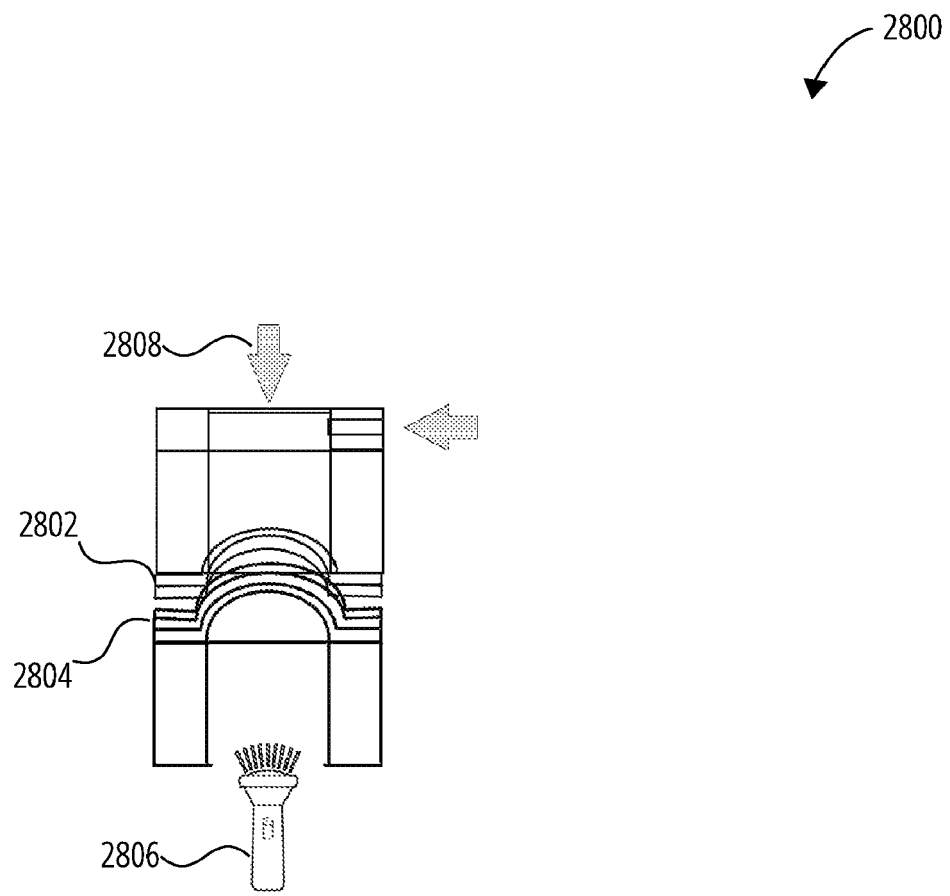
FIG. 28 illustrates a step in a method of making a lens and sensor device according to an embodiment 2800.

In an embodiment, the top layer 2802 and bottom layer 2804 may be bonded together using UV light 2806 as shown in FIG. 28. Pressure 2808 may be applied to the two layers while the UV bonding is done.

Figure 29:
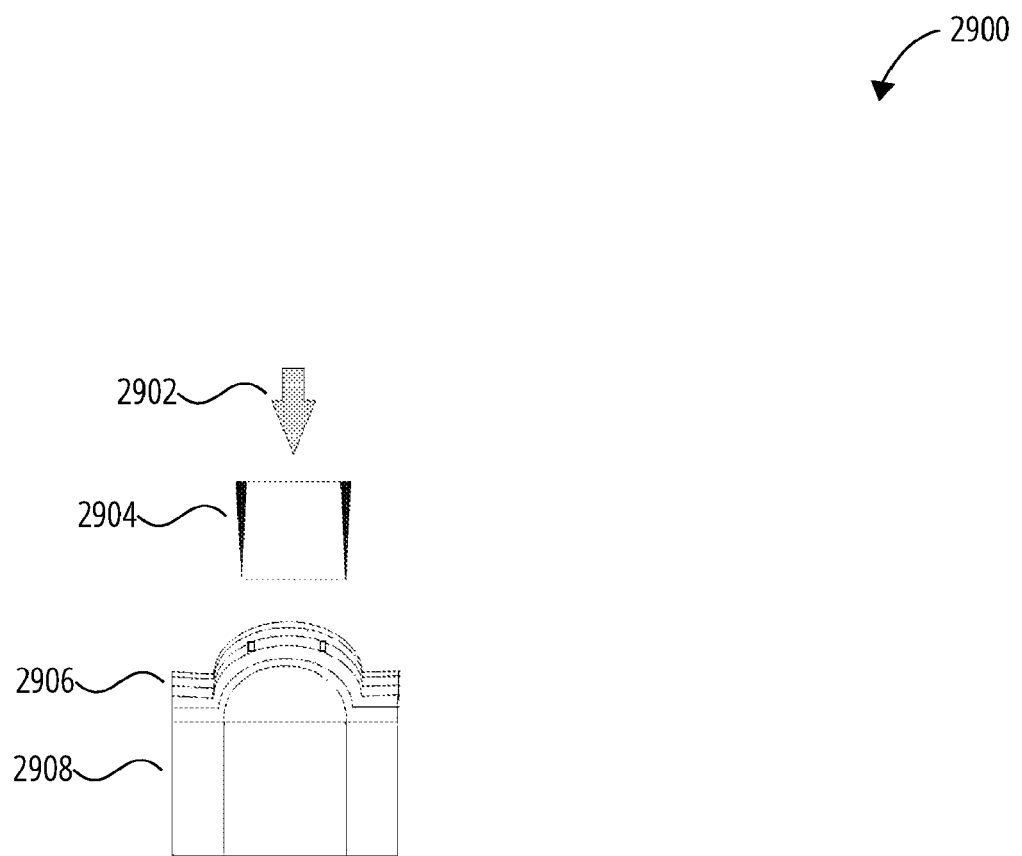
FIG. 29 illustrates a step in a method of making a lens and sensor device according to an embodiment 2900.

In an embodiment, the contact lens with IOP sensor 2906 may be exposed by removing the top mold assembly as shown in FIG. 29. Exposure of the contact lens with IOP sensor 2906 may allow for a punch cutter 2904 to be centered over the lens. The application of force 2902 may cut the contact lens with IOP sensor 2906 away from the curved mold assembly 2908.

In another embodiment, after bonding, the top mold may be removed to allow access of a cylindrical punch cutter. The assembled lens may be cut using the punch and removed from the curved mold. The lens may then be filled with detection fluid and made hydrophilic and may be ready to use.

We now go on to describe various methods of measuring the intraocular pressure based on optical changes in metal-insulator-metal type cavities upon strain.

Figure 30:
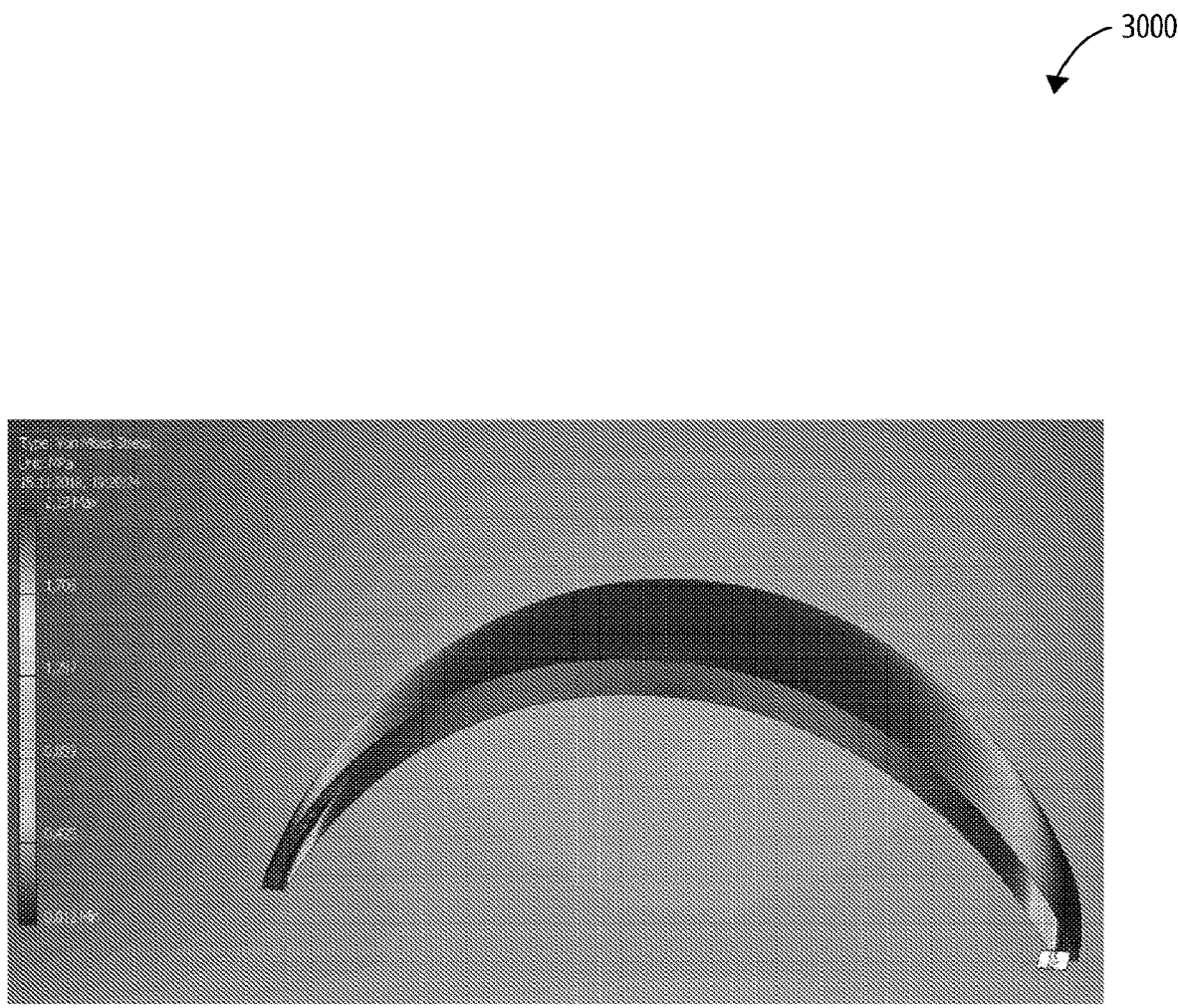
FIG. 30 illustrates a stress model according to an embodiment 3000.

An example model of the strain distribution of an elastomeric contact lens is shown in FIG. 30. As can be seen in the figure, a Von Mises Stress pattern is shown with a scale of the stress on the left of the image. The image is a computer-generated image of an actual contact lens according to an embodiment. The strain can be seen near the edges of the contact lens.

Figure 31:
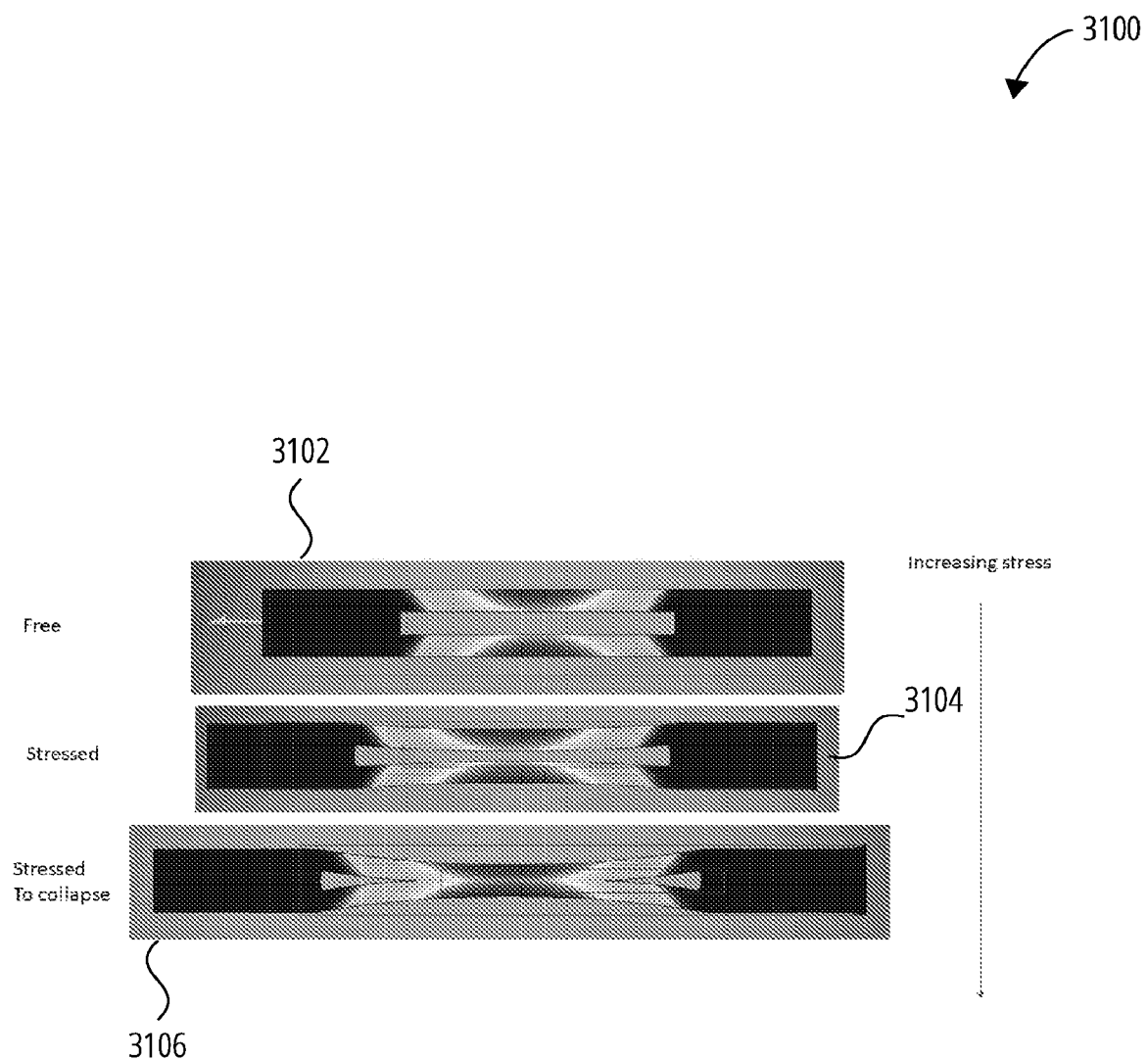
FIG. 31 illustrates a series of stress patterns according to an embodiment 3100.
Figure 32:
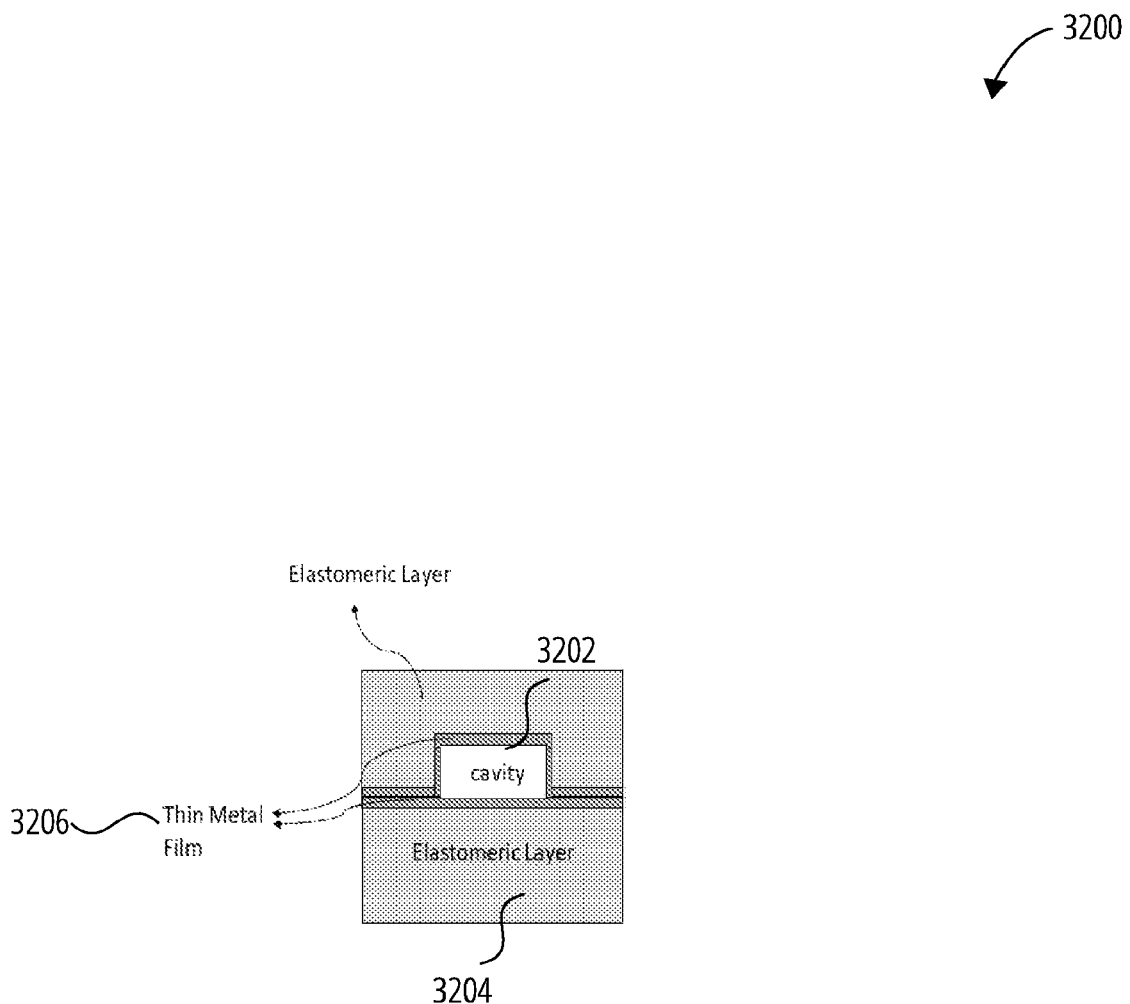
FIG. 32 illustrates a cross section of a metalized cavity according to an embodiment 3200.

In various embodiments, a variety of stress situations may be demonstrated as shown in FIG. 31. A cross section of a free 3102 cavity lens is shown at the top of the drawing page. In another embodiment, a stressed 3104 cavity pattern is shown in the middle. The bottom illustrates a stressed to collapsed 3106 cavity.

In an embodiment, a cross section of a metallized elastomeric rectangular cavity is shown. The cavity 3202 may be coated or surrounded by thin metal film 3206 strips sandwiched between elastomeric layers 3204. This design forms an interferometric structure whose optical properties depend sensitively on the deformation of the cavity.

Figure 33:
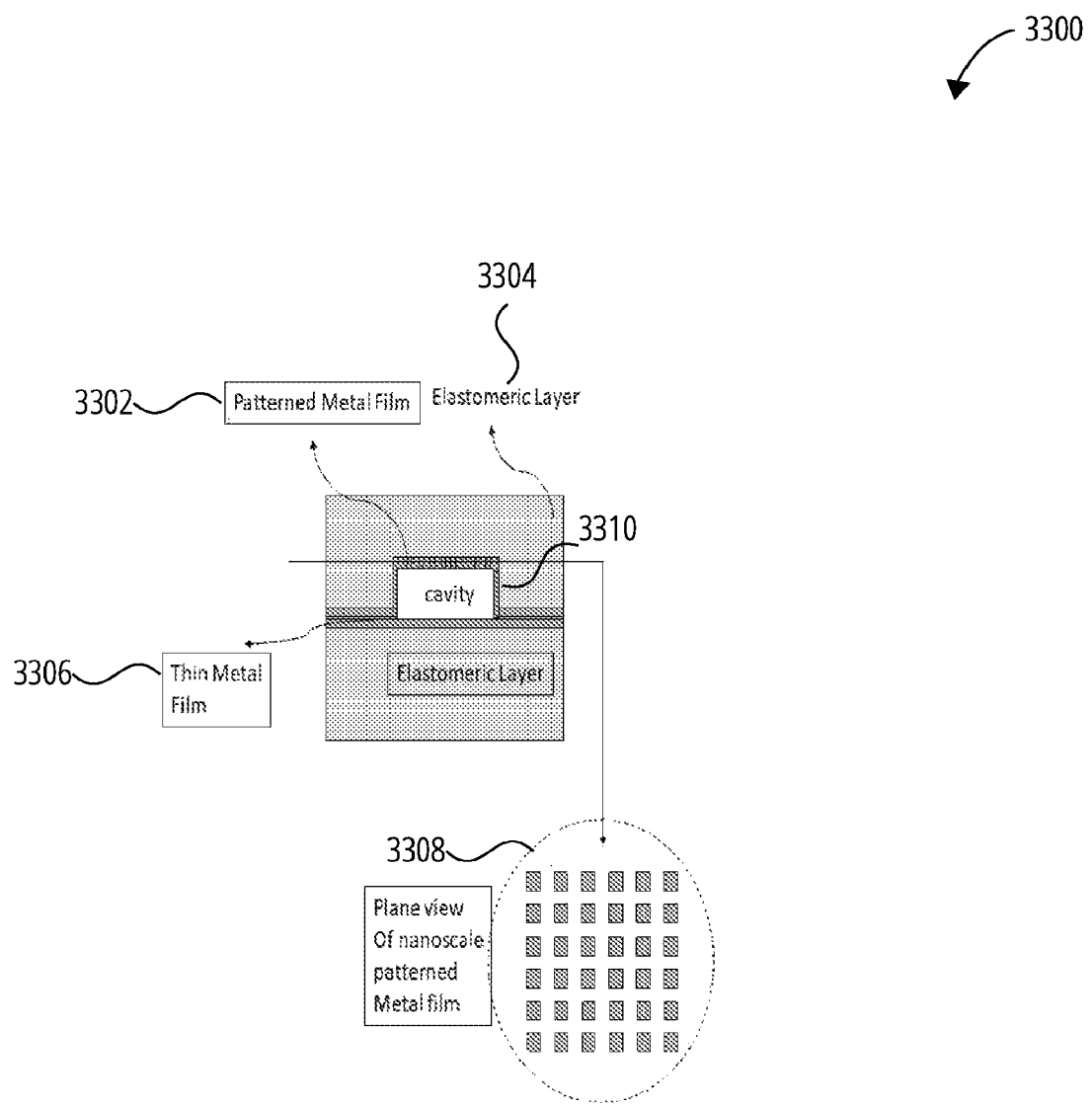
FIG. 33 illustrates a nanoscale pattern film according to an embodiment 3300.

An alternate view of the thin metal film is shown in FIG. 33. In an embodiment, a cavity 3310 is surrounded by a pattern metal film 3302 and a thin metal film 3306. The two metal films may be sandwiched between a pair of elastomeric layers 3304. The pattern metal film 3302 may be a nanoscale patterned metal film. The pattern may help tune the optical properties such as optical resonances and angular response. Periodic or quasi periodic metal patterns with characteristic dimensions ranging from 1 nanometer to 10 micrometers may be used. The size and patterns of the structures may be optimized for improving the optical response at a specific wavelength and angular incidence.

Figure 34:
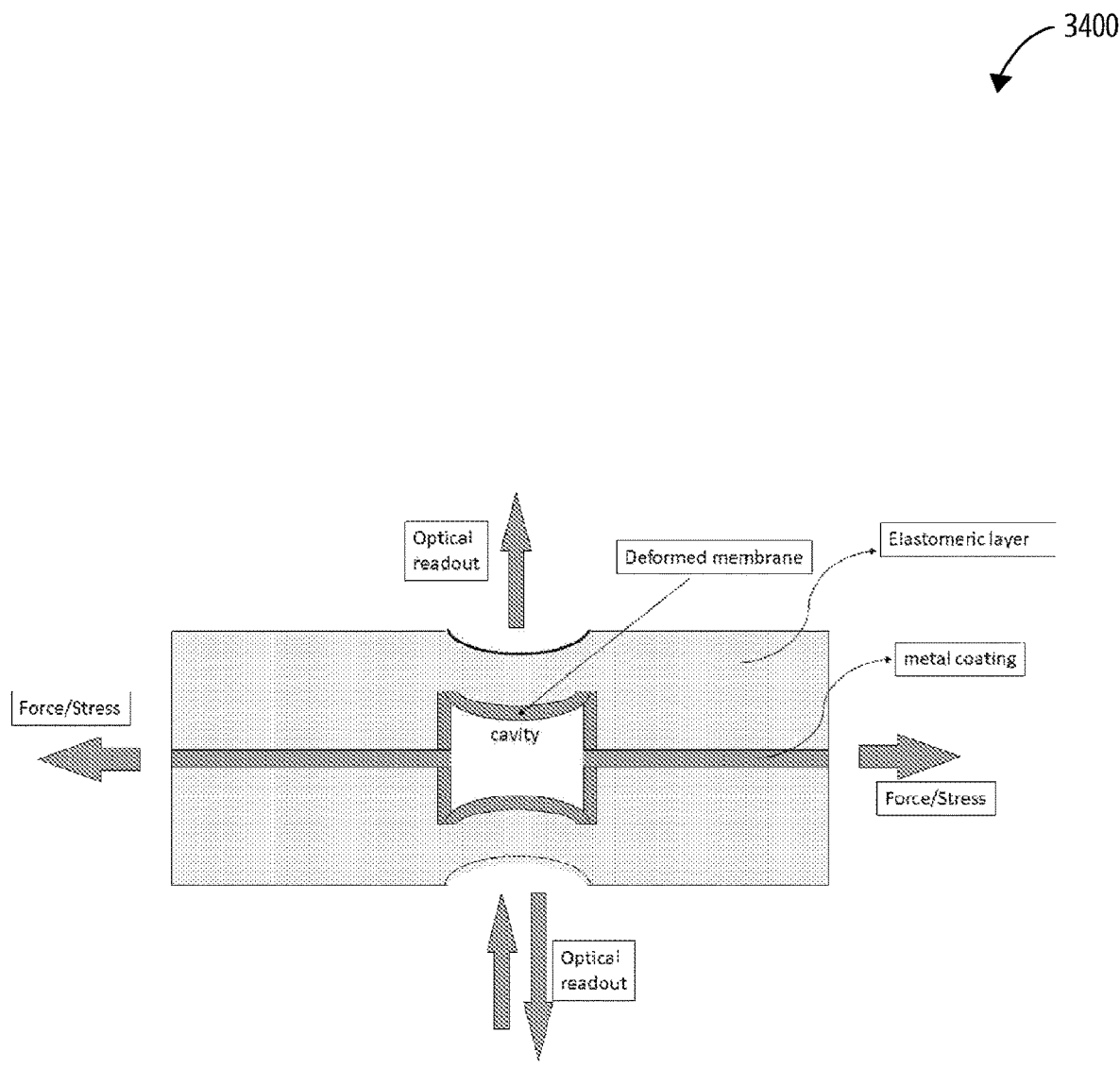
FIG. 34 illustrates a stress deformation example according to an embodiment 3400.

In an embodiment, the cross section of a metallized elastomeric rectangular cavity and deformation under applied stress is shown in FIG. 34. The stress vectors are shown in the horizontal plane, causing the cavity to be pulled to the sides and to compress along the top and bottom. The elastomeric layers provide a flexible medium that may tolerate the various stress and strain forces without compromising the material. The arrows up and down illustrate the vectors of light waves entering and exiting the lens in order to read the level of force, stress or strain on the contact lens.

Figure 35:
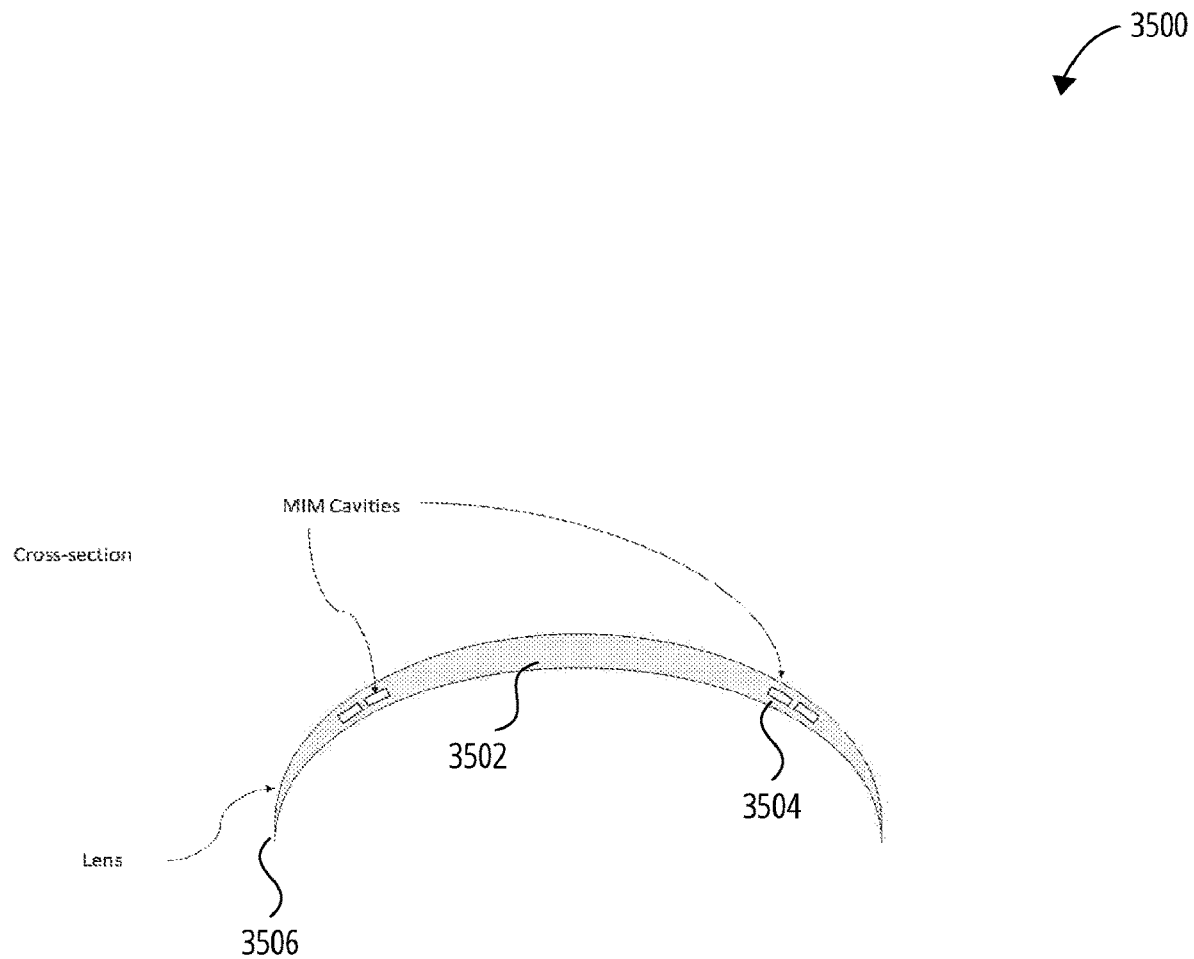
FIG. 35 illustrates a cross section of a lens and sensor region according to an embodiment 3500.

A cross section of an embodiment of the contact lens is shown in FIG. 35. In an embodiment, the contact lens 3506 has a viewing region 3502 and a sensing region 3504. The viewing region may be generally clear and substantially free from microfluidic structures, sensors or other elements that may adversely affect vision. The sensing region 3504 may contain the sensors that respond to changes in the TOP of the eye, sensors that detect stress or strain based on the shape of the eye and so on.

In an embodiment, there may be metal insulator metal (MIM) cavities in the sensing region 3504. The MIM cavities may detect changes in the TOP of the eye, and change shape in response to the changes in IOP. The shape changes may advance or withdraw the fluid-air interface in the micro microfluidic channels, which can be read by an optical sensor.

Figure 36:
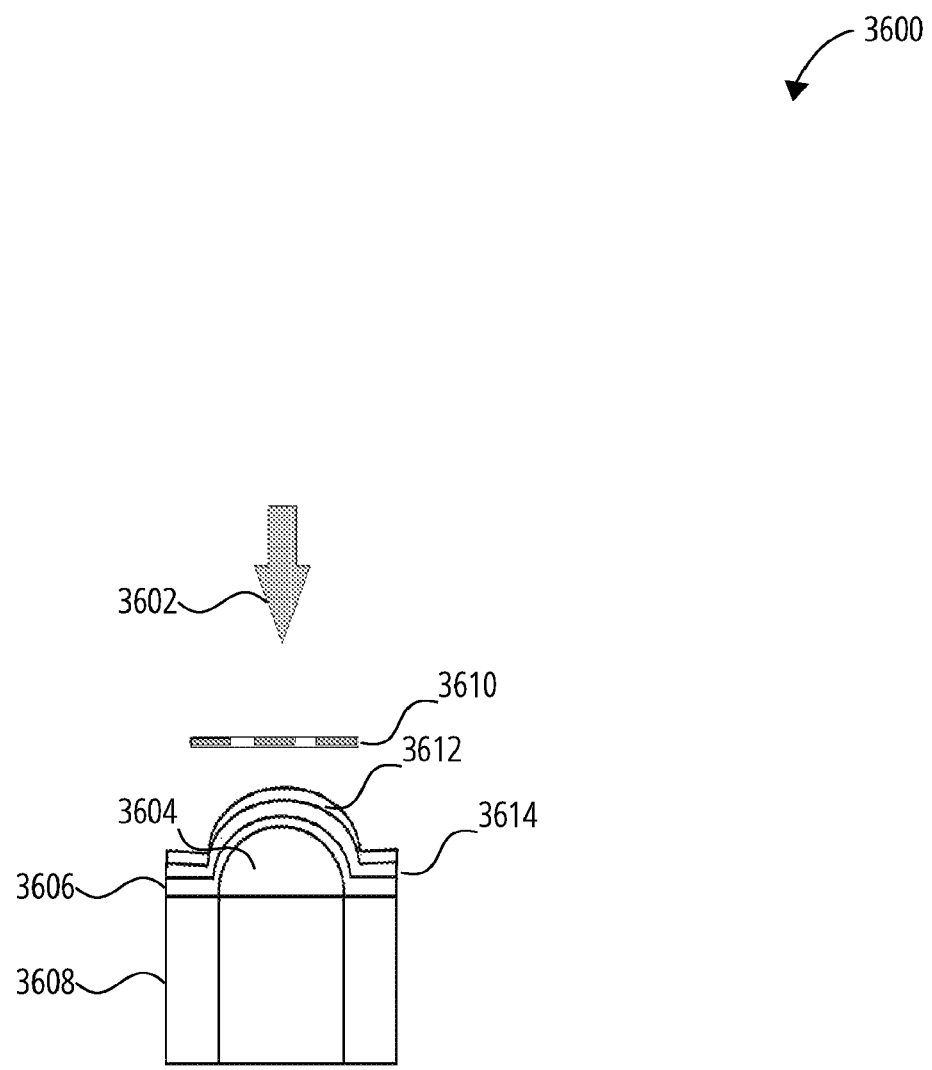
FIG. 36 illustrates a shadow mask according to an embodiment 3600.

In another embodiment, there may be a metallization procedure for the contact lens with IOP sensors as shown in FIG. 36. In an embodiment, a lower base assembly 3608 may hold a curved mold 3604. The curved mold may have a bottom membrane 3606, a UV curable layer 3614 and a metal layer 3612 as shown. Metal deposition 3602 may occur through a shadow mask 3610 to deposit metal on the metal layer 3612. In some embodiments, the deposition may be done by evaporation or sputtering. In other embodiments, the metal layer may be placed on the membrane without a shadow mask 3610, and instead it may be EDM (electrical discharge machining) or micro machined to a particular pattern.

In various embodiments, the bottom membrane 3606, and the UV curable layer 3614 may be any similarly described layer herein.

Figure 37:
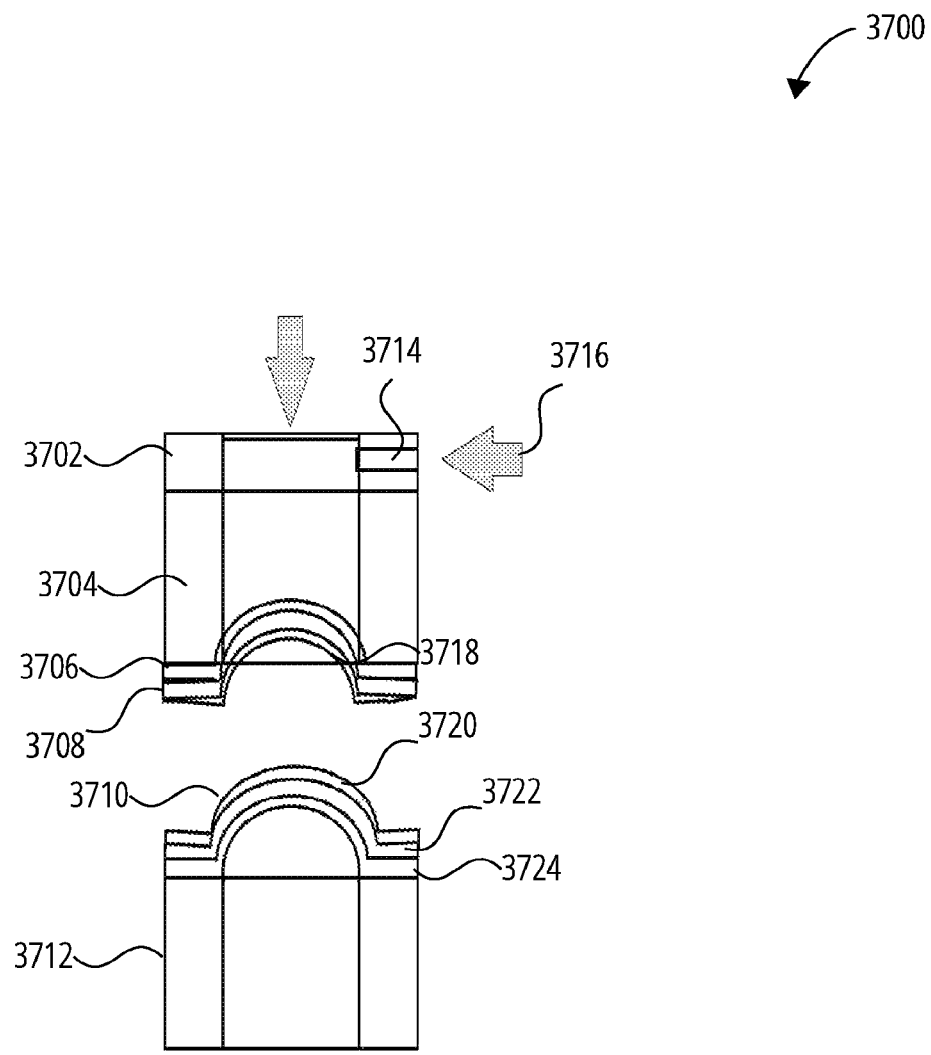
FIG. 37 illustrates an assembly of top and bottom layers according to an embodiment 3700.
Figure 38:
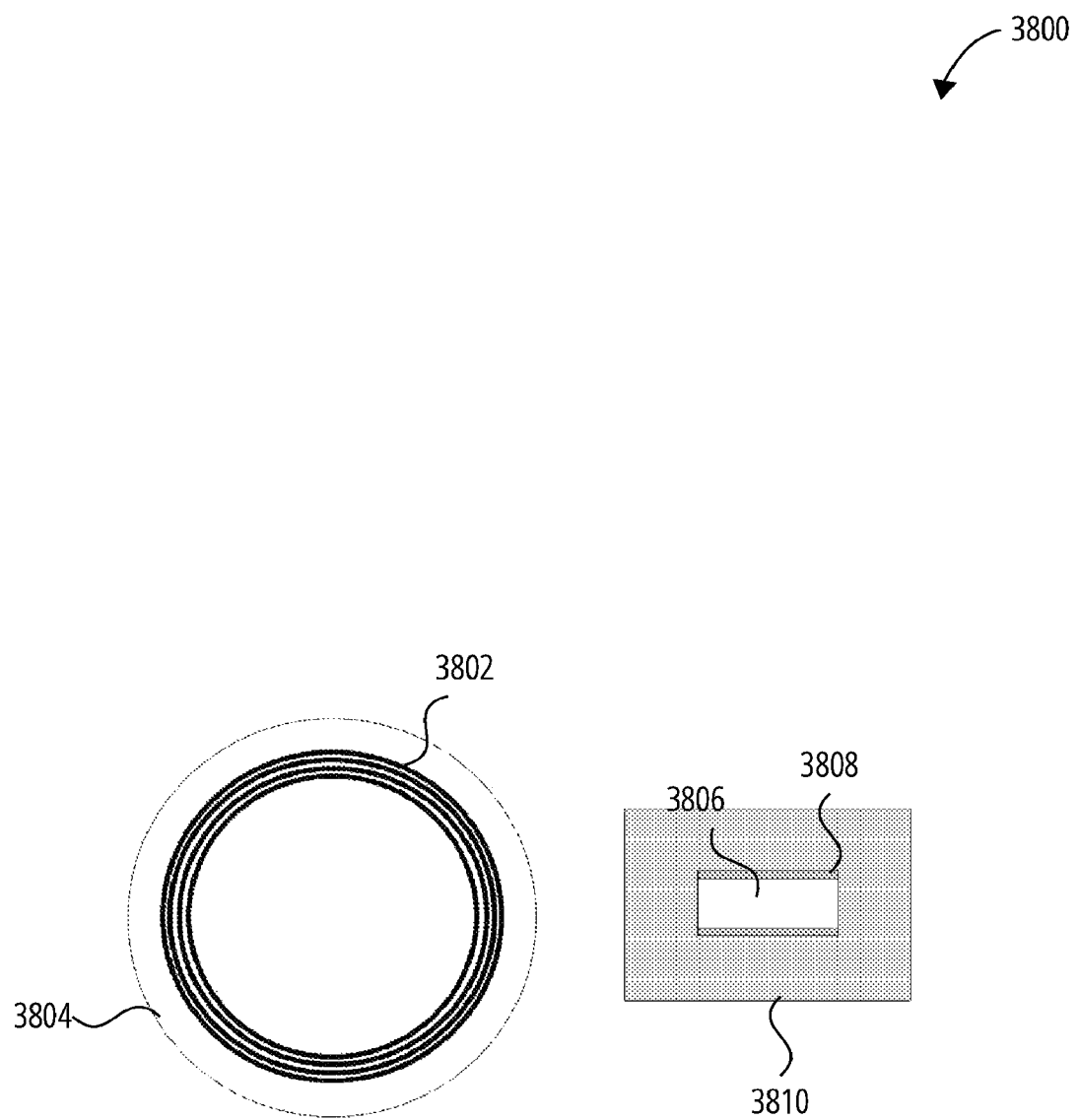
FIG. 38 illustrates an annular sensor component according to an embodiment 3800.

In an embodiment, the assembly of the various layers is shown in FIG. 37. In an embodiment, a holder 3704 may have a pressurizing cap 3702 with an air access hole 3714. The top membrane 3706 may have a UV curable resin layer 3708 and a metal layer 3718. The lower base assembly 3712 may have a thin bottom membrane 3710 that may include a second metal layer 3720, a UC UV curable layer 3722 and a bottom membrane 3724. The thin bottom membrane 3710 composition may sit on a curved mold on the lower base assembly 3712. The top and bottom membranes may be pressed together and bonded to form into an elastomeric contact lens with optical strain sensors.

In an embodiment the contact lens 3810 may have a series metallization cavities 3802. A cross section is shown with the metallization layer 3808, the metallization cavity 3806 and the contact lens 3810. In this embodiment, the strain caused by a change in the IOP of the eye may perturb the cavities and modify the electromagnetic resonances of the ring shaped metallization cavity 3802, causing the rings to act as remote sensing antennas. In an embodiment, the lenses may sense intraocular pressure through a remote radio frequency measurement, similar to the readout of an RF-ID chip.

Figure 39:
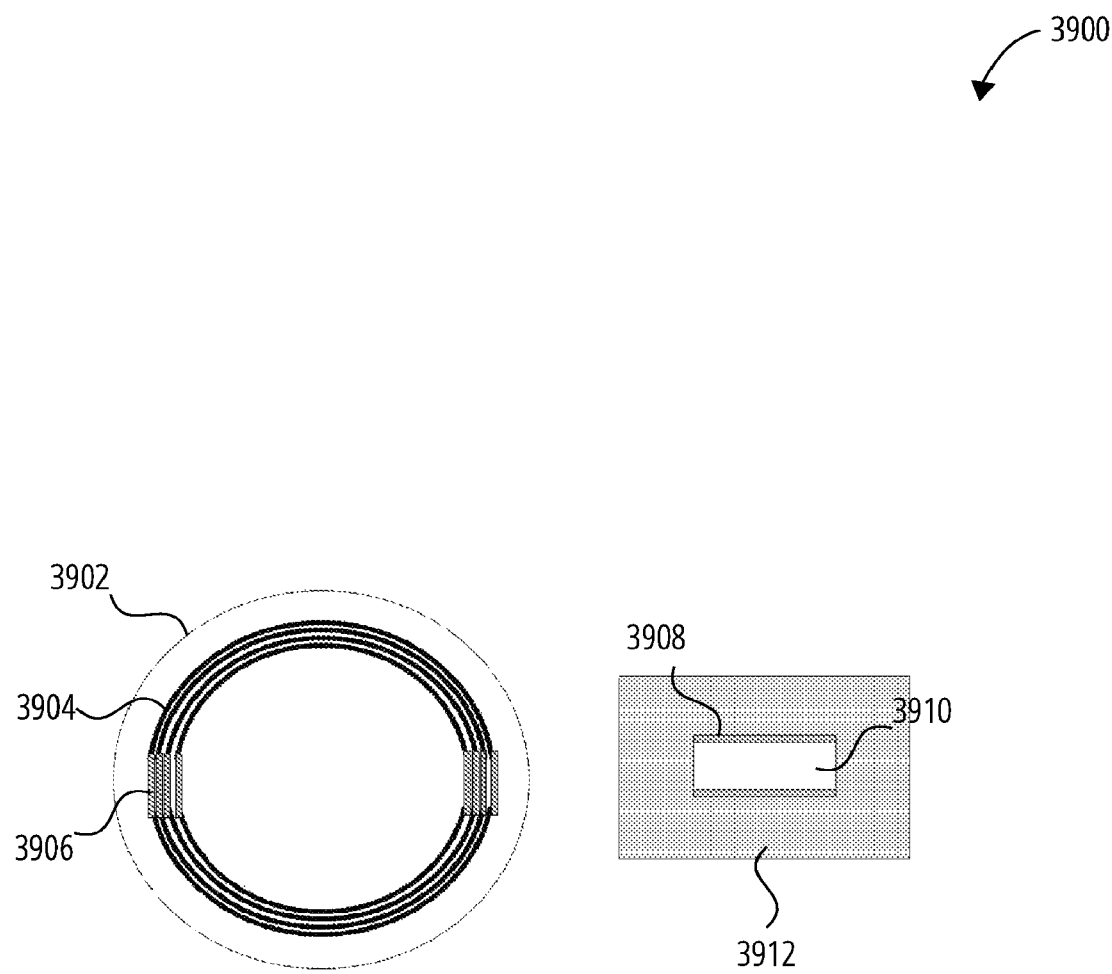
FIG. 39 illustrates an annular sensor component with strain perturbed cavities according to an embodiment 3900.

In another embodiment, the contact lens 3902 may have metallized metalized regions 3904 with cavities 3906 as shown in FIG. 39. Changes in the TOP of the eye may cause strain to perturb the cavities 3906. The alteration of the cavities may modify the electromagnetic resonances of the metalized regions 3904 to act as remote sensing antennas. In this embodiment, the lenses may be used to sense changes in intraocular pressure through remote radio frequency resonance measurement, similar to the readout of a RFID chip.

In an embodiment, a cross section of the metallized metalized regions 3904 is shown. The cross section shows a single cavity 3910 and the metallization layer 3908 on two of the cavity sides. The cavity is imbedded in the contact lens 3912. While this embodiment shows two sides of the cavity with metallization layers, it should be understood that the cavity may have anywhere from 1-4 sides with metallization layers. The cavity may not be a regular polygon, and may have a circular cross section. In such instances the cavity may have any portion of the circumference of the cross section metallized to achieve a similar result as described herein.

Figure 40:
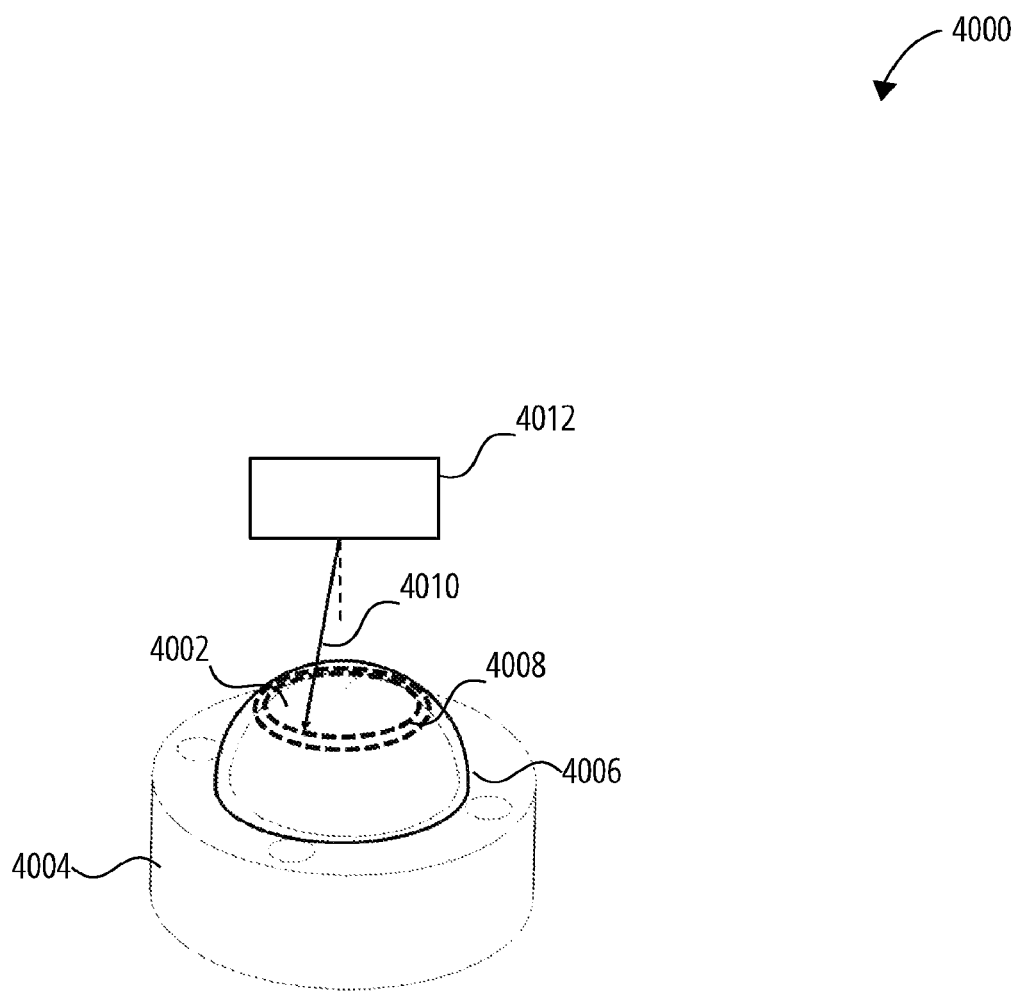
FIG. 40 illustrates a laser system projecting on a membrane according to an embodiment 4000.
Figure 41:
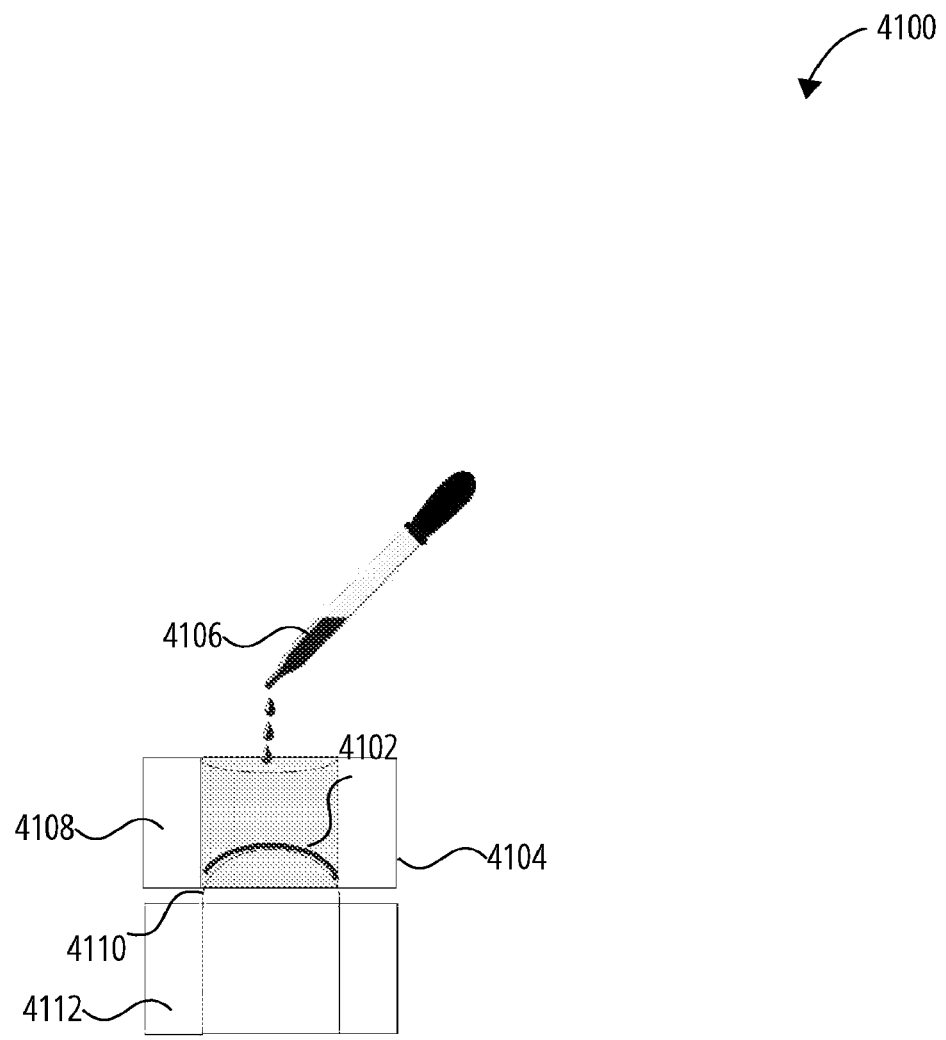
FIG. 41 illustrates creating a mold according to an embodiment 4100.

In still another embodiment, there is an alternative method of making the curved mold 4002 as shown in FIG. 40. In an embodiment, the curved mold 4002 may be coated with a photoresist 4006. A laser projection system 4012 may be used to define by UV exposure 4010, the microfluidic channel patterns 4008 directly onto the curved mold 4002 with photoresist 4006.

In some embodiments, the polymer layer may be made from a photodefinable polymer like SU8. The microfluidic channels may form in concentric rings, a "C" ring around the sensor region with switch back corners to provide continuous channels going around the periphery.

In some embodiments, the microfluidics sensor may use an air reservoir. The height of the air reservoir may be from 1 micron to 1 mm. In some other embodiments the air reservoir height may be from 5 to 500 microns. In still other embodiments, the height of the air reservoir may be from 10 to 200 microns.

In some embodiments, an air reservoir may also be provided. In some embodiments, the air reservoir may have a width of 1 µm to 10 mm. In another embodiment the width may be 10 microns to 1 mm. In still other embodiments, the width of the air reservoir may be between about 30 microns to 200 microns.

In some embodiments, the number of liquid reservoir channels may be between about 1 to 1,000,000. In some other embodiments the number of liquid reservoir channels may be between about 1 to 100. In still other embodiments the number of liquid reservoir channels may be about 1 to 20.

In another embodiment for making the mold, the top side of the curved mold 4110 with microfluidics patterns 4102 may be turned into a mold by filling the top aperture of the holder 4104 with an elastomer 4106. The cylindrical housing 4108 contains the elastomer 4106 which may be cured. The curved mold 4110 may be attached to a lower base assembly 4112.

Figure 42:
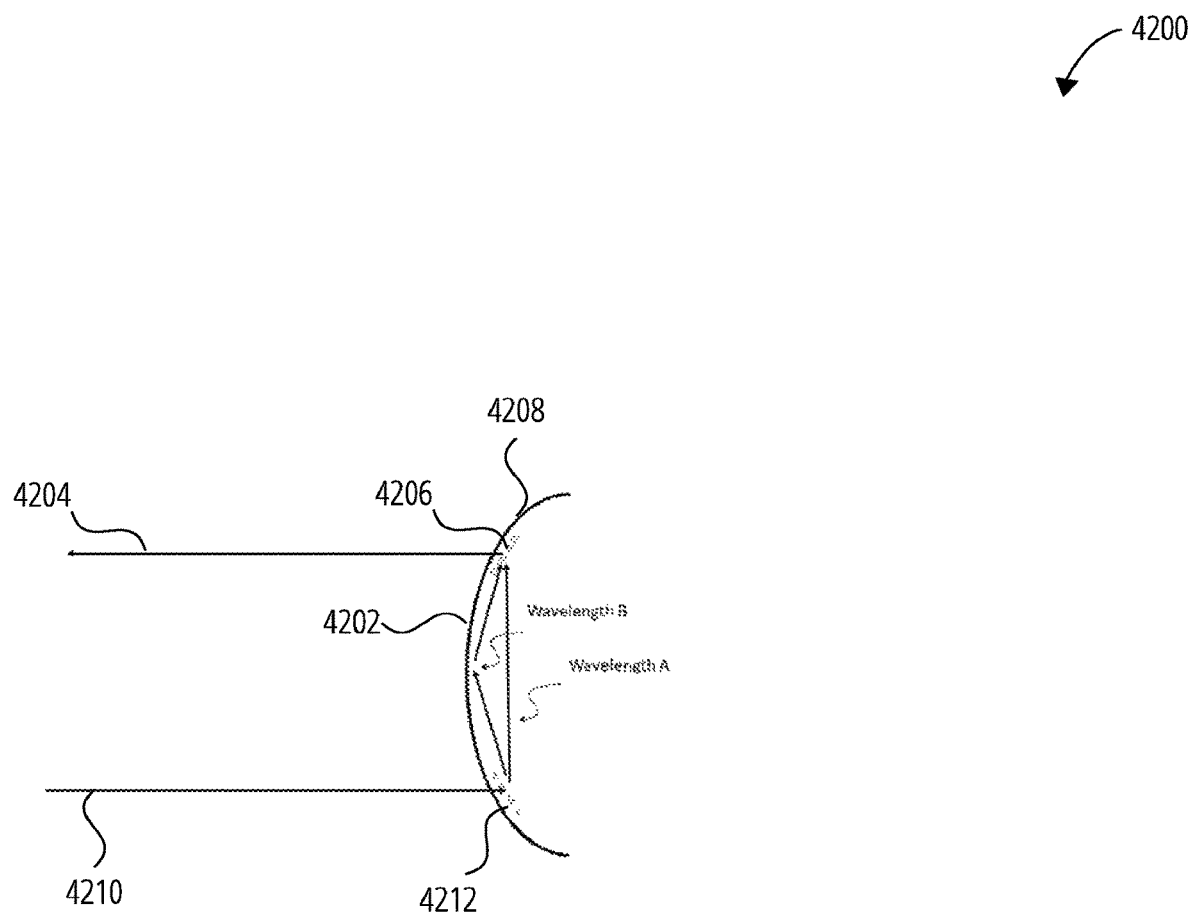
FIG. 42 illustrates light interaction with an optical sensor according to an embodiment 4200.

An alternative method and device for measuring IOP may be seen in an embodiment shown in FIG. 42. In this embodiment, light entering 4210 the eye may pass through a contact lens 4202 resting on the cornea 4208. Some light entering 4210 passes through transmission type grating for the input light 4212 and output light 4206. The input light 4212 diffracts internally, passing through the cornea 4208 or posterior corneal cavity (beyond the iris), and may be outcoupled back as output signal or light exiting 4204 the eye. The light exiting 4204 may be imaged using a regular color or spectrally resolved camera system for intensity and position to extract strain related perturbations in the lens and cornea.

Figure 43:
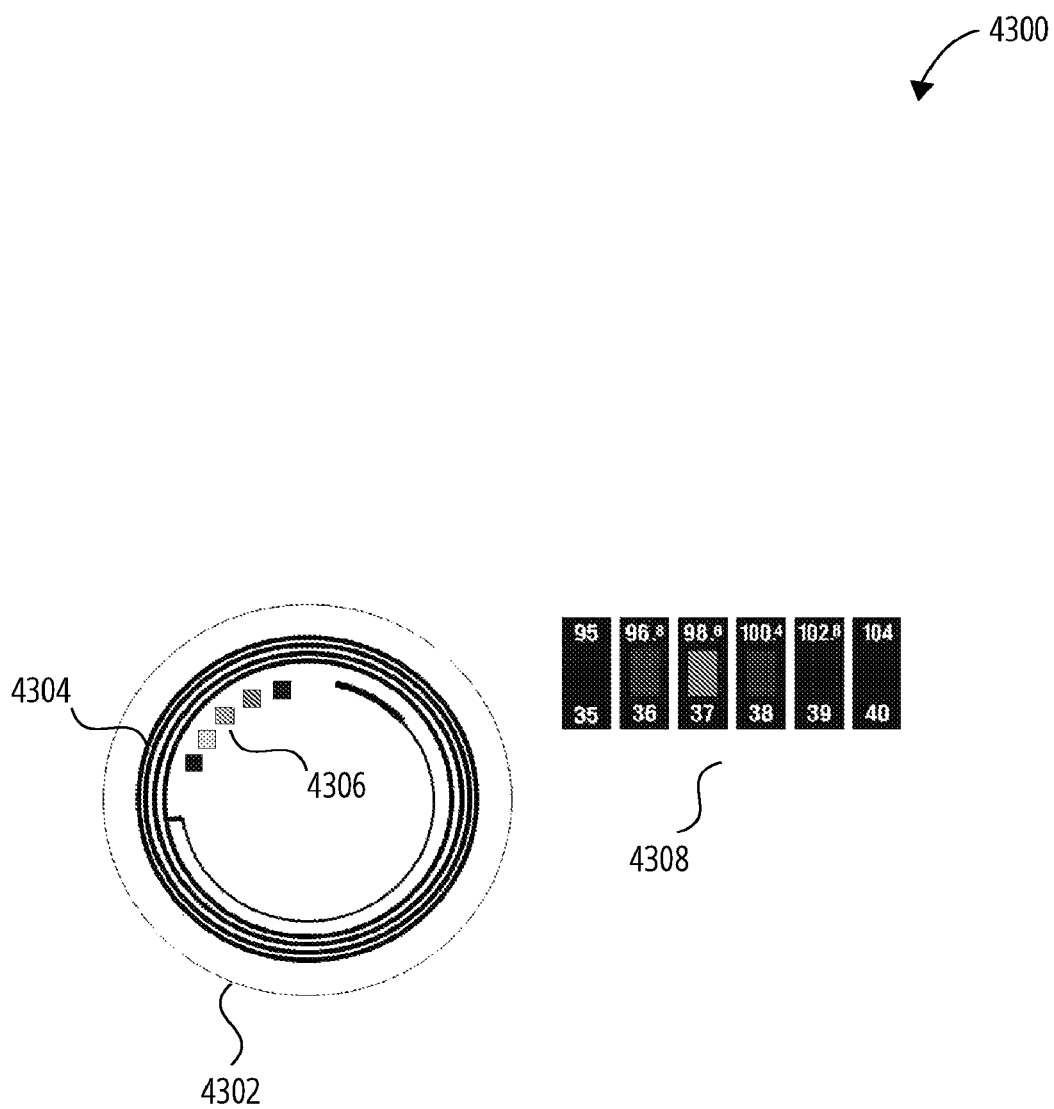
FIG. 43 illustrates a temperature sensor according to an embodiment 4300.

In still another embodiment, a contact lens 4302 may have one or more microfluidics features 4304 and embedded liquid crystal patterns 4306 as shown in FIG. 43. In some embodiments, the embedded liquid crystal patterns 4306 may produce color palettes that may be detected by a camera, such as those on a cell phone or tablet. The color palettes may be read and compared to an optical thermometer array 4308. The liquid crystal optical thermometer array 4308 can be used to measure temperature based on different spots having varying color transition temperatures. The contact lens 4302 with microfluidics features 4304 or other optical features may now supplement for independent temperature measurement by using the embedded liquid crystal patterns 4306. A picture of the lens may yield the device temperature.

Figure 44:
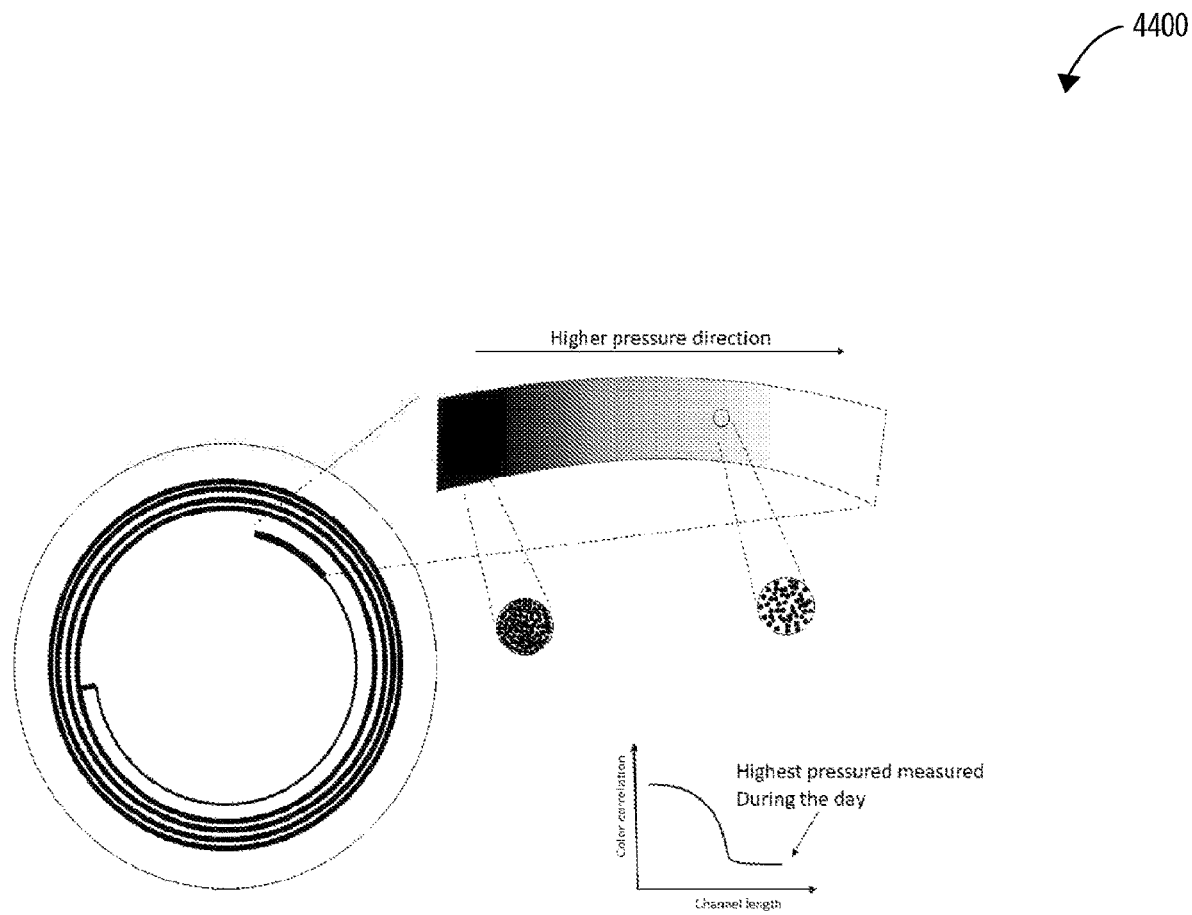
FIG. 44 illustrates pressure sensor according to an embodiment 4400.

In another embodiment, an alternative feature for the contact lens is shown in FIG. 44. In an embodiment, a solution may be mixed with beads or dyes that have low binding affinity. As the eye pressure changes throughout the day, dyes may bind to the channel walls where the solution resides. The longer the walls of the channels may be exposed to the dye, the darker or more intense the color stain on the walls. Based on dwell time, highest, average and standard deviations of the eye pressure may be calculated from the color correlation map (shown with the spectrum from dark to light).

Figure 45:
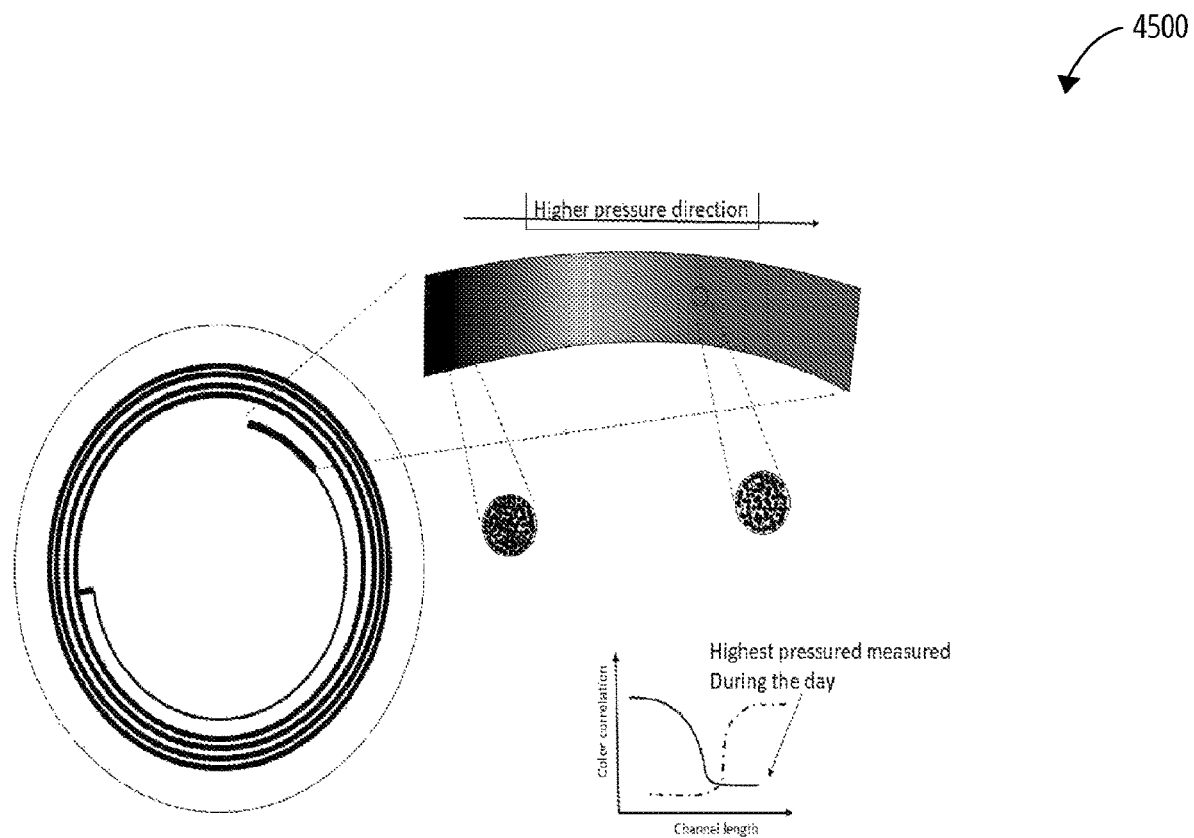
FIG. 45 illustrates pressure sensor according to an embodiment 4500.

In yet another embodiment, an additional feature for a contact lens with a sensor is shown in FIG. 45. In an embodiment, the lens' micro channels may be filled with red dyes (or beads). The red dye (or bead) may be withdrawn after an incubation period. The dyes may leave red residue through the channel with the dyes bound to channel walls. Later, a solution with blue dyes may be loaded to the channel for eye pressure measurement. An imaging method may be used to retrieve color correlation through the channel for red and blue colors. Using a correlation algorithm, it may be possible to calculate the highest, average, and standard deviations of the eye pressure throughout the day and night.

Figure 46:
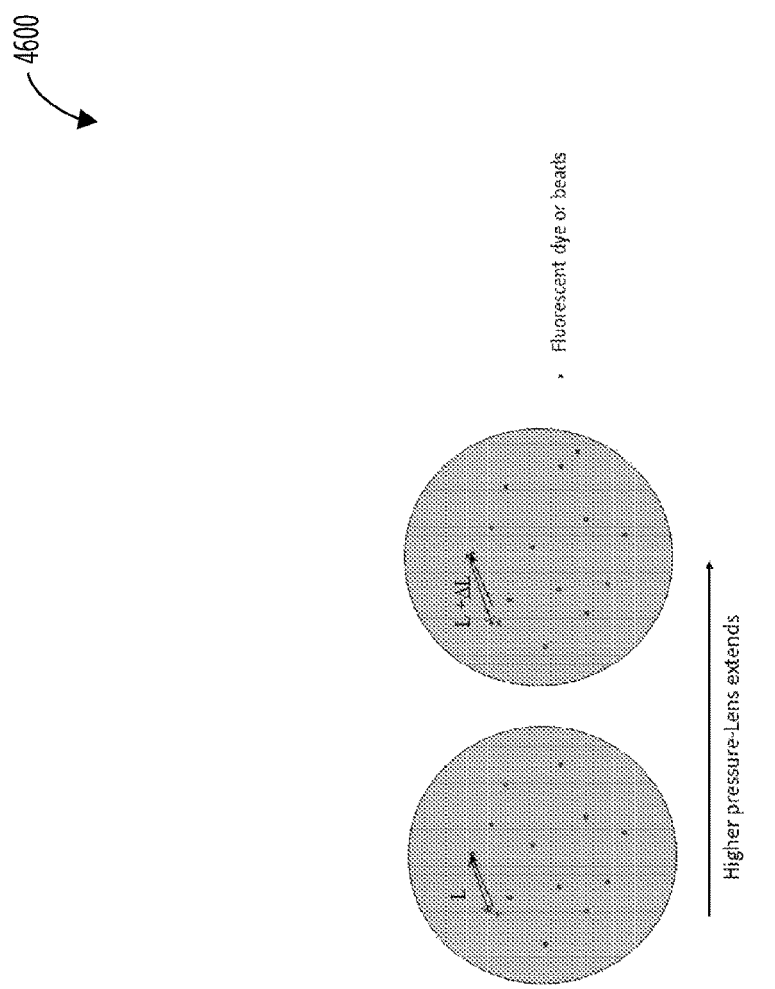
FIG. 46 illustrates pressure sensor according to an embodiment 4600.

In another embodiment, beads may be embedded in the contact lens, as shown in FIG. 46. The fluorescent beads may have a diameter between 10 nm to 1 mm. In some embodiments the diameter may be 1 to 250 microns. In still other embodiments the diameter of the beads may be between 20 to 100 microns. The beads may be placed in the contact lens. The contact lens may be made of a transparent elastic material. The beads may be localized with various imaging techniques using an excitation source such as a UV or Blue or Green LED light and using a camera with an emission band bass filter, or a smartphone adapter having the same. Beads may be located with high accuracy by fitting point-spread-functions to 2-D gaussian functions and distances between the beads may be determined with micrometer accuracy using such data processing. As the eye pressure changes, the lens may be extended or compressed, and the beads' relative positions may change due to the changes in the curvature of the eye. The strain on the contact lens may be determined for each bead pair and overall pressure change may be accurately calculated.

In some embodiments, the distance between beads may be between 1 micron to 10 cm. In another embodiment the distance between beads may be between 10 microns and 1 mm. In still another embodiment, the distance between beads may be between 50 to 500 microns.

Figure 47:
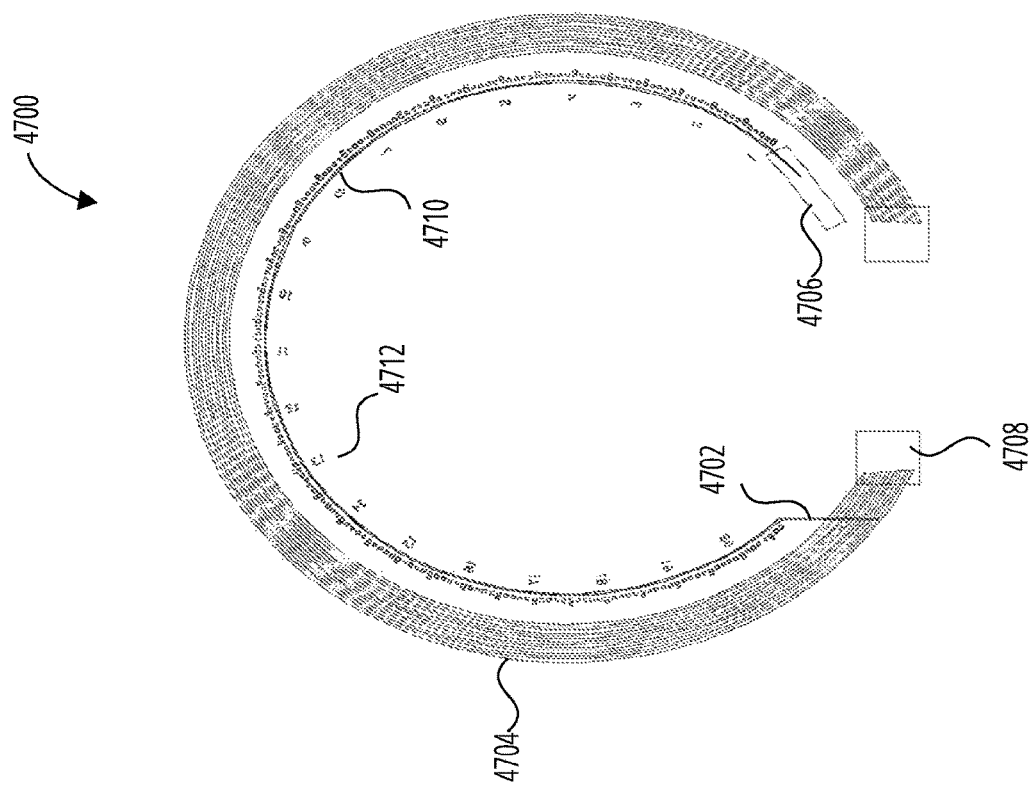
FIG. 47 illustrates a sensing region with a "C" shaped sensing channel according to an embodiment 4700.

In an embodiment, a C-shaped sensing channel 4704 may be used in place of one or more annular ring channels as shown in FIG. 47. The sensing channel 4704 may have a fill port for adding liquid, and a reporting channel 4702 for indicating the level of intraocular pressure the eye is experiencing. An air reservoir 4706 provides the air to form the gas-air interface in the microfluidics channel 4710. A scale 4712 may be present on the sensing region. In an embodiment, the scale may be viewed using a camera, such as on a cell phone, and the image may show the level of IOP according to the location of the liquid-gas interface on the microfluidics channel 4710.

The advantages of the present disclosure include, without limitation, a robust process for making of highly sensitive wearable contact lens sensors that require no electrical power or circuits and can be monitored remotely by a simple camera like one found in a mobile phone.

Various aspects of the disclosure are now provided:
1. A method aspect of producing a planar mold, the method comprising:
    fabricating a planar substrate from a material; and creating one or more reliefs on the planar substrate
wherein the one or more reliefs will create one or more microfluidic channels in a membrane sheet; and
wherein the material is optionally made from silicon or a silicon composite.

2. A method aspect of producing a mold for use in the fabrication of a contact lens sensor, the method comprising:
placing a liquid material on a planar mold, the liquid material being capable of changing from a liquid state to a substantially solid state, wherein the planar mold will impart one or more microfluidic channels to the liquid material as the material transitions to the substantially solid state, the substantially solid state of the material forming a membrane sheet;
centering a holder on to the membrane sheet;
excising a portion of the membrane sheet, the portion of the membrane sheet having the microfluidic channels, the portion of the membrane being a membrane template;
clamping the membrane template between the holder and a base assembly, the base assembly having an aperture;
removing the holder from the base assembly such that the membrane template remains on the base assembly;
pressing the base assembly to a curved mold, such that the membrane template is pressed against the curved mold;
filling at least a portion of the base assembly aperture with additional liquid material;
curing the liquid material so the liquid material has a curve matching the curved mold; and
separating the curved mold from the membrane template.

3. The method of aspect 2, wherein the transition of the liquid material to a substantially solid state involves curing the material for a period of time.

4. The method of aspect 2, wherein the liquid material is a polymer.

5. The method of aspect 2, wherein the liquid material is an elastomeric substance.

6. The method of aspect 2, wherein the method is a lithographic process.

7. The method of aspect 2, wherein one or both of the holder and the base assembly are configured in a substantially tube shape.

8. The method of aspect 7, wherein one or both of the holder and base assembly are substantially cylindrical.

9. The method of aspect 2, wherein one or both of the holder and the base assembly are an annular ring.

10. The method of aspect 2, wherein the membrane template substantially matches a footprint of the holder.

11. The method of aspect 2, wherein the excising of the membrane template is done with a laser.

12. A method aspect of producing a mold for a contact lens with a sensor, the method comprising:
coating a curved mold with a photoresist;
curing the photoresist;
creating a predefined pattern in the photoresist;
developing a patterned surface in the photoresist; and
pouring an elastomer on top of the predefined pattern surface; and
curing the photoresist to produce the mold.

13. A method aspect for the production of a sensor and lens apparatus, the method comprising:
forming a bottom membrane layer by coating a curved mold with a liquid elastomer;
curing the bottom membrane layer;
treating the bottom membrane layer with plasma to make an elastomeric surface hydrophilic and promote adhesion of a UV curable polymer;
coating the bottom membrane with a UV curable polymer;
imprinting a microfluidic layers on the UV curable polymer using an etched mold;
making a top membrane layer by pouring elastomer on to a second curved mold;
curing the top membrane layer;
releasing the top membrane layer after curing;
performing a plasma treatment on the inside of the top membrane;
coating the inside of the top membrane with UV curable polymer, and partially curing to solidify the UV curable polymer;
placing the top membrane onto a pressurizing chamber;
bonding the top and bottom membranes together to form a contact lens and sensor template;
cutting the contact lens and sensor template to size, the cutting forming an abrupt edge on the contact lens; and
applying a UV curable polymer to the abrupt edge of the contact lens to form an atraumatic edge.

14. The method of aspect 13, wherein the making of a hydrophilic elastomeric surface further comprises curing the surface with a UV curable polymer from a backside.

15. The method of aspect 13, where in the coating is done by spinning the mold as the material is added on to the mold, or layers of polymer on the mold.

16. An apparatus aspect for measuring the intraocular pressure of an eye, the apparatus comprising:
an elastomeric contact lens body with a sensor region; and
a plurality of metallized Fabry-Perot optical interference cavities, the cavities distributed in the sensor region;
wherein changes of shape and reflected light cause changes in the contact lens' shape due to changes in intraocular pressure.

17. The apparatus of aspect 16, wherein the changes in the contact lens shape may be sensed remotely.

18. The apparatus of aspect 16, wherein the changes in the contact lens shape may be sensed indirectly.

19. An apparatus aspect for measuring the intraocular pressure of an eye, the apparatus comprising:
an elastomeric contact lens body with a sensor region; and
a plurality of metallized cavities distributed in a sensor region of the contact lens body;
wherein the plurality of metallized cavities act as mechanically variable capacitors and resonating antennas within the contact lens;
wherein the plurality of metallized cavities change electromagnetic resonant response properties upon changes in intraocular pressure, by changing in capacitance or by changes in direct electrical contact between different parts of the antennas.

20. The apparatus of aspect 19, wherein the intraocular pressure of an eye may be sensed remotely.

21. The apparatus of aspect 19, wherein the intraocular pressure of an eye may be sensed indirectly.

22. An apparatus aspect for measuring the intraocular pressure (IOP) of an eye, the apparatus comprising:
an elastomeric contact lens body with a sensor region;
a plurality of embedded transmission type gratings, the grating permitting external light into the posterior corneal cavity;
a plurality of input and output coupling gratings for routing of the external light;

wherein the coupling condition on angle of incidence and wavelength of light can be used to calculate the strain exerted on the contact lens.

23. The apparatus of aspect 22, wherein the strain exerted on the contact lens may be used to determine the corneal deformation due to intraocular pressure.

24. An apparatus aspect for measuring the intraocular pressure of an eye, the apparatus comprising:
an elastomeric contact lens body having a sensor region; and
a plurality of fluorescent beads embedded into the sensor region.

25. The apparatus of aspect 24, wherein the plurality of fluorescent beads are sized between 0.01 μm to 600 μm in diameter.

26. The apparatus of aspect 24, wherein the plurality of fluorescent beads are sixed between 0.1 μm and 400 μm.

27. The apparatus of aspect 24, wherein the plurality of fluorescent beads are scattered in the contact lens with an average distance between the fluorescent beads of 1 μm to 10 mm.

28. The apparatus of aspect 24, wherein the separation of the plurality of fluorescent beads changes based on changes in the intraocular pressure of the eye.

29. The apparatus of aspect 28, wherein the separation of the fluorescent beads is determined by a mobile phone app on a mobile phone with a camera.

30. A system aspect for determining changes in intraocular pressure over time, the system comprising:
an elastomeric contact lens with a sensor region; and
a plurality of microfluidic channels dispersed within the sensor region, the channels containing a density sensitive material capable of adhering to the microfluidic walls; and
an optical reader for reading the changes in the density sensitive material;
wherein the changes in density of the density sensitive material corresponds to changes in the intraocular pressure of the eye; and
wherein reading the optical density changes on the walls can be used to calculate intraocular pressure.

31. The system of aspect 30, wherein the density sensitive material is a dye.

32. The system of aspect 30, wherein the density sensitive material is a bead.

33. The system of aspect 30, wherein the optical reader is a mobile phone.

34. The system of aspect 30, wherein the density sensitive material is absorbed into the surface of the microfluidic channels.

35. The system of aspect 34, wherein the density sensitive absorption by the microfluidic channels corresponds to changes in intraocular pressure.

36. An apparatus aspect for measuring the intraocular pressure of an eye, the apparatus comprising:
an elastomeric contact lens with a sensor region; and
a plurality of liquid crystal thermometers embedded in the sensor region; wherein the liquid crystal thermometers change color due to corneal temperature changes.

37. The apparatus of aspect 36, wherein the color can be detected remotely.

38. The apparatus of aspect 36, wherein the color can be detected indirectly.

What is claimed is:

1. A method for the production of a contact lens and sensor apparatus, the method comprising: forming a bottom membrane layer by coating a curved mold with a liquid elastomer; curing the bottom membrane layer; treating the bottom membrane layer with plasma to make an elastomeric surface hydrophilic and promote adhesion of a first UV curable or heat curable polymer; coating the bottom membrane layer with the first UV curable or heat curable polymer; imprinting at least one microfluidic layer on the first UV curable or heat curable polymer using an etched mold; making a top membrane layer by pouring elastomer on to a second curved mold; curing the top membrane layer; releasing the top membrane layer after curing; performing a plasma treatment on the inside of the top membrane layer; coating an inside of the top membrane layer with the first UV curable or heat curable polymer, and partially curing to solidify the first UV curable or heat curable polymer; placing the top membrane layer onto a pressurizing chamber; bonding the top and bottom membrane layers together to form a contact lens and sensor template; cutting the contact lens and sensor template to size, the cutting forming an abrupt edge on the contact lens; and applying a second UV curable or heat curable polymer to the abrupt edge of the contact lens to form an atraumatic edge.

2. The method of claim 1, wherein the making of the hydrophilic elastomeric surface further comprises curing the surface with a third UV curable or heat curable from a backside.

3. The method of claim 2, wherein the third UV curable or heat curable polymer comprises a different UV curable or heat curable polymer than the first UV curable or heat curable polymer and the second UV curable or heat curable polymer.

4. The method of claim 1, wherein coating the bottom membrane layer is done by spinning the curved mold as the first UV curable or heat curable polymer is added onto the curved mold, or wherein coating the inside of the top membrane layer is done by spinning the second curved mold as the first UV curable or heat curable polymer is added onto the second curved mold.

5. The method of claim 1, further comprising: adding a solution into the microfluidic layer, the solution mixed with beads or dyes with a low binding affinity.

6. The method of claim 4, where in the beads are fluorescent beads having a diameter between 10 nm up to 1 mm.

7. The method of claim 6, wherein the fluorescent beads are between 0.01 μm to 600 μm in diameter.

8. The method of claim 5, wherein adding a solution into the microfluidic layer comprises adding a first color solution mixed with beads or dyes; and adding a second color solution with dyes.

9. The method of claim 8, further comprising retrieving a color correlation of the first color solution and the second color solution via imaging.

10. The method of claim 9, further comprising calculating one or more of a high, average, or standard deviation of an eye pressure throughout a 24 hour cycle via a correlation algorithm.

11. The method of claim 5, further comprising imaging the beads via one or more of UV light, blue LED light, or green LED light.

12. The method of claim 11, wherein imaging comprises imaging using an emission band bass filter with one or more of a camera or a smartphone adapter.

13. The method of claim 5, further comprising locating the beads by fitting point-spread-functions to 2-D gaussian functions.

14. The method of claim 1, further comprising:
arranging a sensor region around a viewing region of the contact lens.

15. The method of claim 1, wherein the imprinting of the at least one microfluidic layer further comprises:
imprinting a liquid reservoir and an air reservoir.

16. The method of claim 1, wherein the first UV curable or heat curable polymer and the second UV curable or heat curable polymer comprise different UV curable or heat curable polymers.

* * * * *